(12) United States Patent
Greenberg et al.

(10) Patent No.: US 6,301,498 B1
(45) Date of Patent: Oct. 9, 2001

(54) METHOD OF DETERMINING CAROTID ARTERY STENOSIS USING X-RAY IMAGERY

(75) Inventors: Roy K. Greenberg, Rochester; Waldemar Celes; Donald Greenberg, both of Ithaca, all of NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/293,016

(22) Filed: Apr. 16, 1999

Related U.S. Application Data
(60) Provisional application No. 60/082,265, filed on Apr. 17, 1998.

(51) Int. Cl.[7] .................................................. A61B 5/05
(52) U.S. Cl. ............................................................ 600/425
(58) Field of Search ..................................... 600/425, 431

(56) References Cited

U.S. PATENT DOCUMENTS

| | | | |
|---|---|---|---|
| 5,285,786 | * | 2/1994 | Fujii ...................................... 600/425 |
| 5,357,550 | * | 10/1994 | Asahina et al. ...................... 600/525 |
| 5,458,126 | * | 10/1995 | Cline et al. .......................... 600/425 |

\* cited by examiner

*Primary Examiner*—William E. Kamm
(74) *Attorney, Agent, or Firm*—Jaeckle Fleischmann & Mugel, LLP

(57) ABSTRACT

A method and apparatus for generating a three-dimensional shape of an artery comprising the step of obtaining at least one angiographic X-ray image of an artery cross section, so that there are lines that define the walls of the artery which have data representing X-ray intensity that can be used to determine artery thickness; gathering the data and inputting that data into a computer; using the data to create a three-dimensional image of the artery.

11 Claims, 28 Drawing Sheets

Current methods of measuring carotid stenosis

Intensity lumen function over a real x-ray image.

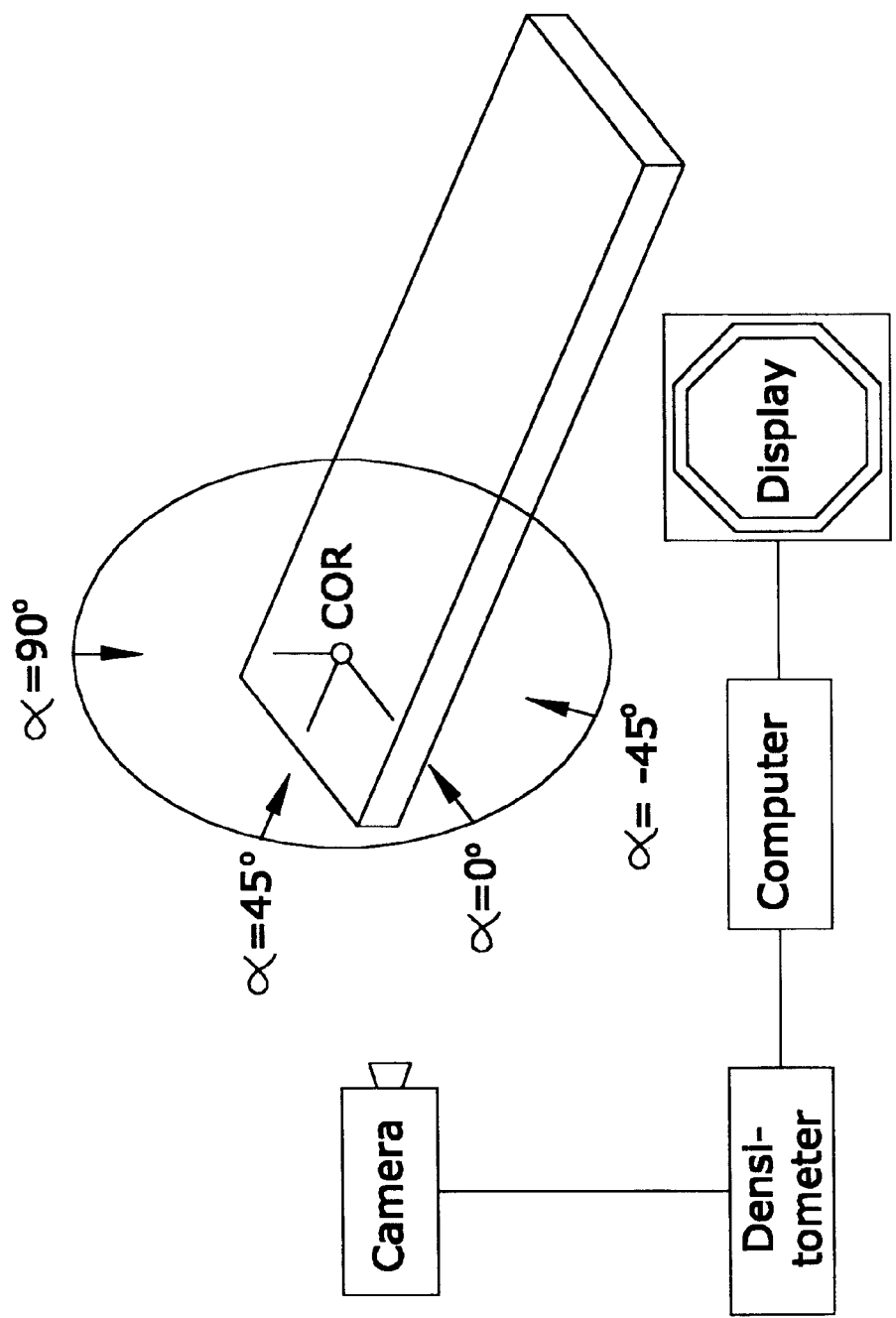

Unknown cross-section and corresponding lumen functions.

Initial cross-section fitted in lumen function boundries.

Scaled lumen functions.

First iteration: upward reconstruction based on x-ray at 0°.

First iteration: downward reconstruction base on x-ray at 0°.

First Iteration: blended reconstruction based on x-ray at 0°.

Second iteration: upward reconstruction based on x-ray at 90°.

Second iteration: downward reconstruction base on x-ray at 90°.

Second iteration: blended reconstruction based on x-ray at 90°.

3D MODEL
COMPUTER MODEL:
VERTICAL COORDINATE
FROM Y= -14 TO Y= 14

INTERPOLATING MESH

KEY SECTIONS

SIMULATED X-RAYS OF COMPUTER MODEL

RECONSTRUCTED 3D MODEL

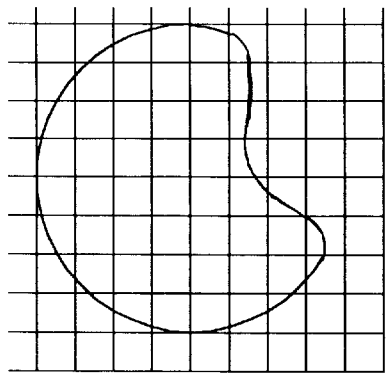
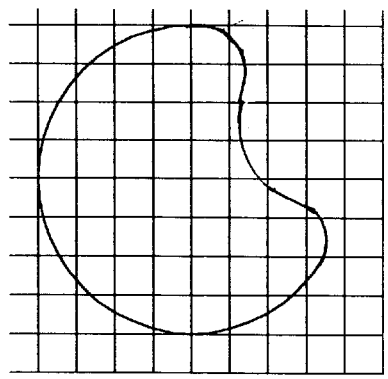
y=-4
y=4
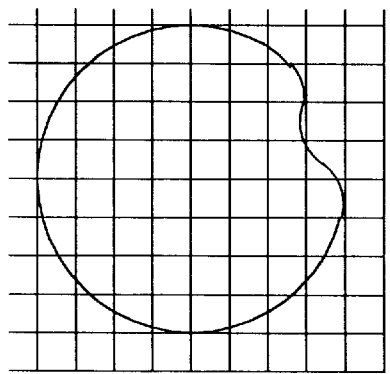
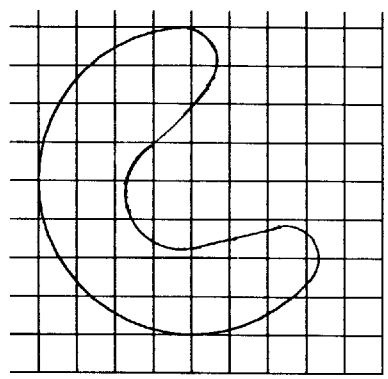
y=-6
y=0
CROSS-SECTIONS
FIG.5f
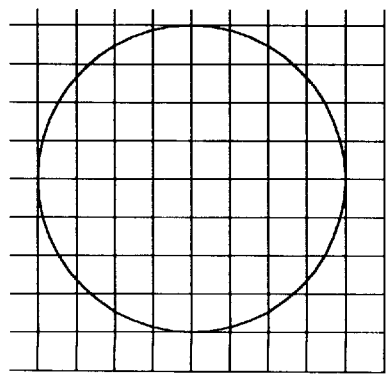
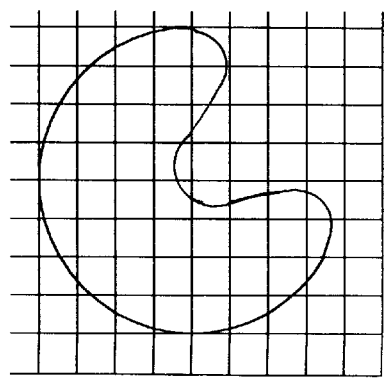
y=-8
y=-2

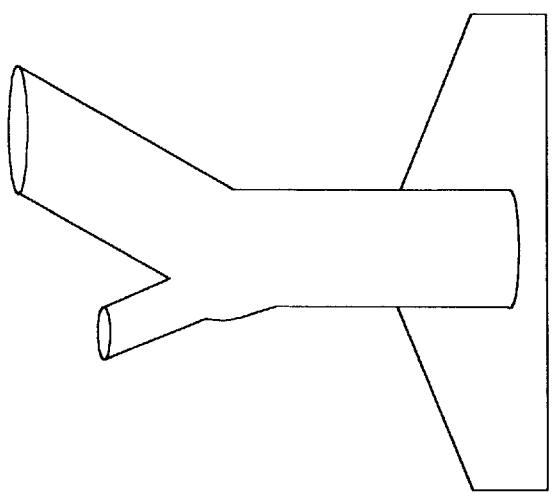
FIG. 6c — 3D MODEL — Y-SHAPE COMPUTER MODEL: VERTICAL COORDINATE FROM Y= -14 TO Y= 14
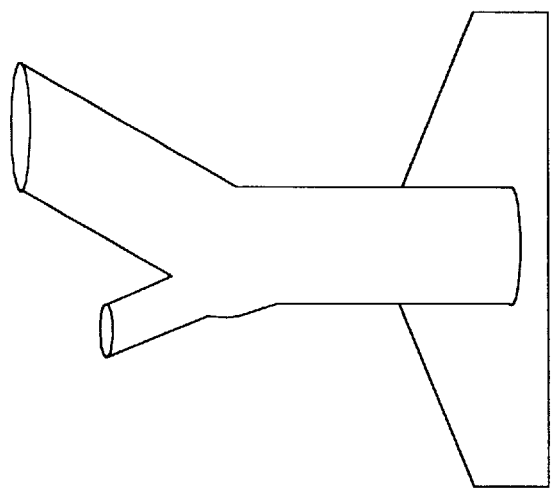
FIG. 6b — INTERPOLATING MESH
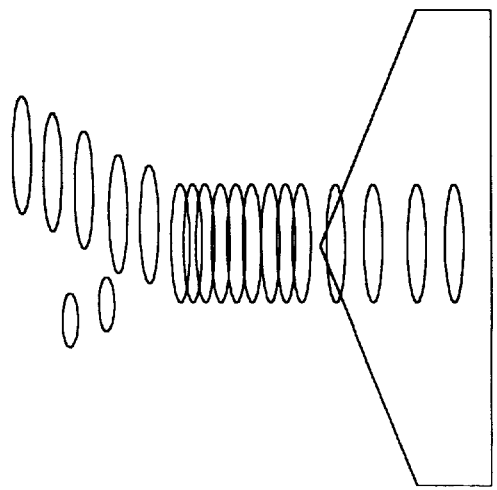
FIG. 6a — KEY SECTIONS

SIMULATED X-RAYS OF COMPUTER MODEL

RECONSTRUCTED 3D MODEL y=-4
 y=4
 y=-6
 y=0
 y=-8
 y=-2

CROSS-SECTIONS

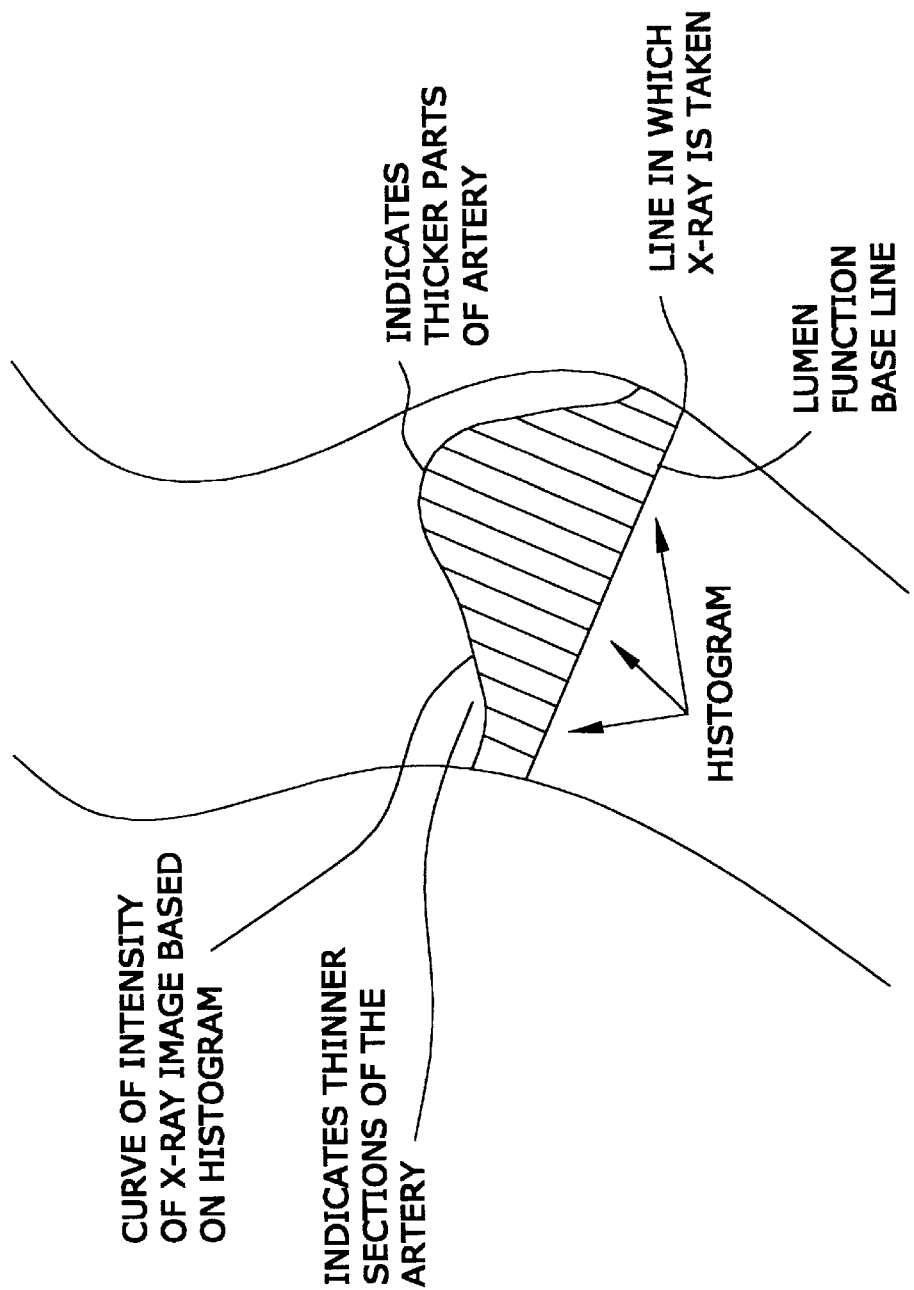

| Section | Original Area | Reconstructed Area | Area Error % | Reconstruction Error % |
|---|---|---|---|---|
| y = 12 | 47.60 | 46.80 | 1.7 | 1.4 |
| y = 10 | 47.62 | 46.94 | 1.4 | 1.3 |
| y = 8 | 47.61 | 46.85 | 1.6 | 1.3 |
| y = 6 | 46.95 | 46.02 | 2.0 | 1.5 |
| y = 4 | 40.46 | 39.24 | 3.0 | 1.6 |
| y = 2 | 29.60 | 28.42 | 4.0 | 3.1 |
| y = 0 | 23.46 | 23.14 | 1.4 | 2.8 |
| y = -2 | 32.62 | 32.25 | 1.1 | 3.0 |
| y = -4 | 40.26 | 39.83 | 1.1 | 2.0 |
| y = -6 | 49.12 | 48.49 | 1.3 | 1.5 |
| y = -8 | 48.79 | 47.79 | 2.0 | 1.2 |
| y = -10 | 48.32 | 47.58 | 1.5 | 1.2 |
| y = -12 | 48.79 | 47.55 | 2.5 | 1.2 |

FIG.13

Table 1: Original and reconstructed C-shape-cross-section model comparison.

| Section | Original Area | Reconstructed Area | Area Error % | Reconstruction Error % |
|---|---|---|---|---|
| y = 12 | 32.29 | 32.50 | 0.7 | 2.5 |
| y = 10 | 31.88 | 31.91 | 0.1 | 1.8 |
| y = 8 | 31.89 | 31.66 | 0.7 | 1.9 |
| y = 6 | 8.78 & 31.83 | 8.50 & 31.48 | 3.2 & 1.1 | 2.5 & 1.4 |
| y = 4 | 9.00 & 26.25 | 8.73 & 25.73 | 3.0 & 2.0 | 2.9 & 2.9 |
| y = 0 | 32.97 | 32.79 | 0.5 | 2.3 |
| y = -2 | 36.05 | 36.39 | 0.9 | 2.3 |
| y = -4 | 35.29 | 34.79 | 1.4 | 1.7 |
| y = -6 | 34.12 | 33.96 | 0.5 | 1.7 |
| y = -8 | 36.69 | 36.44 | 0.7 | 1.9 |
| y = -10 | 37.84 | 37.62 | 0.6 | 1.7 |
| y = -12 | 37.82 | 37.73 | 0.2 | 1.8 |

Table 2: Original and reconstructed bifurcated model comparison.

FIG. 14

METHOD OF DETERMINING CAROTID ARTERY STENOSIS USING X-RAY IMAGERY

This application claims the benefit of U.S. Provisional Application 60/082,265 filed Apr. 17, 1998 entitled "X-ray Imaging for Carotid Artery Reconstruction." The provisional application is hereby incorporated by reference in its entirety.

BACKGROUND OF THE INVENTION

Carotid arteries supply the head and neck with blood. There is a right common carotid artery and a left common carotid artery. Both the right and left common carotid arteries divide into an external carotid artery and an internal carotid artery. The external common carotid arteries supply blood to the face, scalp, and most of the neck and throat tissue. The internal common carotids supply blood to the brain and other tissue generally accessible from within the scalp, as the eyes. The carotid arteries may suffer from a condition known as stenosis.

Carotid stenosis is an abnormal condition characterized by the constriction or narrowing of these vital arteries by a substance known as plaque, that prevents proper circulation of the blood to the head. Plaque is a localized area of atherosclerosis, that deposits of lipids (fatty substances) and a proliferation of fibrous connective tissue on the inner walls of the arteries. Carotid stenosis may sometimes be treated by a procedure known as endarterechtomy, that is the surgical removal of the innermost layer of the carotid arteries. Endarterechtomy is performed to clear a major artery that may be blocked by the accumulation plaque. In scientific and routine medical work, the measurement of carotid artery stenosis (the measurement of how much the carotid arteries have been constricted due to plaque deposits) has been used to determine whether a patient is likely to benefit from endarterechtomy. High-risk patients may be identified by finding "severe" lesions (a pathological change in body tissue) of the carotid arteries using a very strict method of measurement of stenosis. An article by Allan J. Fox, "How to Measure Carotid Stenosis," Radiology, 186:316–318 (1993) teaches how to identify high risk patients based on the measurement of the extent of stenosis of the carotid arteries (the article is hereby incorporated by reference).

An Angiography-based diagnosis is current standard for determining the extent of carotid stenosis. Angiography is a special X-ray procedure that takes pictures ("angiograms") of blood vessels. This diagnostic technique makes use of a radiopaque contrast medium, which is a chemical substance that does not permit the passage of X-rays or other radiant energy. Angiography is the X-ray visualization of the internal anatomy of the heart and/or blood vessels after the introduction of a radiopaque contrast medium into the blood. The contrast medium may be injected into an artery or a vein or introduced into a catheter (a hollow tube) inserted in a peripheral artery. The catheter is a small, flexible, hollow tube about the size of a thin strand of spaghetti. The radiologist carefully threads it into the blood vessel and guides it to the area to be studied. The radiologist watches the catheter moving through the blood vessels on a special X-ray television screen. When the catheter reaches the site under investigation, X-ray dye is injected through the catheter. An X-ray image of the artery shows the irregularities or blockages.

The term "angiogram" refers to the radiographic image of a blood vessel produced by angiography. Angiograms have darkened areas that represents open channels in blood vessels. These darkened areas are caused by the contrast medium blocking the passage of X-rays. The main problem with using angiography to measure the extent of carotid stenosis is that current methods misuse angiograms. Diagnoses of carotid stenosis using angiograms are currently based on a single two-dimensional X-ray. Using current techniques, although up to four X-ray projections are usually taken from different angles using current techniques, each is only a two-dimensional image. The four selected angiograms provide limited three dimensional information about carotid stenosis. When multiple projections are used, the one which provides the greatest percentage of stenosis is usually adopted. Such methods may significantly underestimate stenosis extent because a single two-dimensional image of an angiographic silhouette cannot accurately depict complex luminal shapes (shapes relating to the tubular cavity of the arteries). An article by Topol and Nissen demonstrates the problems of using angiographic silhouettes to determine complex luminal shapes. See E. J. Topol and S. E. Nissen. "Our preoccupation with coronary luminalogy: The dissociation between clinical and angiographic findings in ischernic hear disease." Circulation, 92(8):2333–2342, October 1995 (this material is hereby incorporated by reference).

The NASCET (North American Symptomatic Carotid Endarterectomy Trial) and the ECST (European Carotid Surgery Trial) are the most known methods to measure carotid stenosis. See FIG. 1. To fully understand the NASCET and ECST methods, see Peter M. Rothwell, Rod J. Gibson, el al, "Equivalence of Measurement of Carotid Stenosis: A Comparison of Three Methods on 1001 Angiograms," Stroke (American Heart Association, Inc.), 25(12):2435–2439, 1994 (this material is hereby incorporated by reference). The NASCET and ECST methods both indicate the degree of stenosis as a percentage reduction in vessel diameter. The minimum diameter of the arteries caused by stenosis (which is the maximum point of blood constriction) ($D_{minimum}$) is compared to another diameter that represents the normal diameter of the carotid arteries when the patient is healthy ($D_{reference}$), to obtain the change in diameter of the vessel as a percentage (% D). The following general formula is used by both the NASCET and ECST methods:

$$\%D = \frac{D_{reference} - D_{minimum}}{D_{reference}} \times 100\%$$

$D_{minimum}$, the minimum diameter of the carotid arteries, represents the "residual lumen." (A "lumen" is the interior space within the artery.) A residual lumen is the part of the channel in the carotid arteries at the point of a lesion that remains open after the onset of carotid stenosis.

The reference point ($D_{reference}$) differs for the NASCET and ECST methods. In the NASCET formula, as seen in FIG. 1, the reference point diameter ($D_{reference}$) is taken along a point of the internal carotid artery in a healthy area well beyond an area of the bulb that was caused by stenosis ($D_{internal\ carotid\ beyond\ bulb}$). The cross-sectional diameter beyond the bulb caused by stenosis is assumed to be approximately the diameter of the carotid arteries at the point of stenosis prior to the onset of stenosis. In the ECST formula, as seen in FIG. 1, the reference point diameter ($D_{reference}$) is the estimated normal lumen diameter at the site of the lesion ($D_{estimated}$), based on a visual impression of where the normal artery wall was before development of the stenosis. FIG. 1 illustrates these formulas.

NASCET method:

$$\%D = \frac{D_{internal\ carotid\ beyond\ bulb} - D_{minimum}}{D_{internal\ carotid\ beyond\ bulb}} \times 100\%$$

ECST method:

$$\%D = \frac{D_{estimated\ normal\ lumen\ diameter} - D_{minimum}}{D_{estimated\ normal\ lumen\ diameter}} \times 100\%$$

Both the NASCET and ECST methods are highly inaccurate because they try to measure a 3D geometric property based on one two-dimensional view of the artery silhouette. The results of both NASCET and ECST formulas have no physical meaning because a narrowing of the artery section cannot be measured by simply observing the reduction in diameter of the artery without a 3D analysis. Still, one can estimate the degree of stenosis by analyzing the cross-sectional area reduction of the artery at the point of the lesion where the artery walls are narrowed. While analyzing the cross-sectional area of reduction of the artery to estimate the extent of stenosis is useful, it is less accurate than a full-scale three-dimensional analysis.

In order to determine the reduction of the cross-section of the arteries, one can assume circular cross-section lesions and calculate the stenosis degree as the percentage of area reduction. For more information on assuming a circular cross-sectional lesion to determine the degree of stenosis, see, D. Delaere, C. Smets, P. Suetens, and G. Maxchal, "Knowledge-based system for the three-dimensional reconstruction of blood vessels from two angiographic projections," *Med. and Biol. Eng. and Comput.*, November 1991 (this material is hereby incorporated by reference). The formula to calculate the degree of stenosis as the percentage of area reduction of the carotid arteries (assuming circular cross-sectional lesions) is:

$$\%A = \frac{D_{reference}^2 - D_{minimum}^2}{D_{reference}^2} \times 100\%$$

where % A is the percent area reduction of the carotid arteries, $D_{minimum}$ represents the point of maximum carotid stenosis, and $D_{reference}$ is the diameter of the carotid arteries at a given reference point.

SUMMARY OF THE INVENTION

X-ray images provide more information than just the two-dimensional outline of the artery as provided by the silhouette. As can be seen in FIG. 2, the X-ray images of the arteries do not form a pure silhouette with the image of the arteries uniformly filled with black. Instead, some of the areas of the arteries fall on a spectrum from very dark to gray.

This variance in the darkness of the image of the arteries provides useful three-dimensional information about the shape of the arteries which, to date, has not been exploited. These areas of darkness reveal the thickness of the artery. The darker the shade of the artery at a particular point, the thicker the luminary structure. In this way, the "intensity variation" (or fluctuation of the intensiveness of the X-ray image) provides depth information about the arteries. Ultimately, each angiographic X-ray image provides not only two-dimensional information provided by the silhouette, but three-dimensional information of the thickness of the artery based on the shades of darkness in the X-ray image. Our invention, unlike prior art devices, makes use of the three-dimensional information by X-ray intensity variation, as well as the two-dimensional information provided by the silhouette.

The darker images, representing thicker lumenal areas of the arteries, are made in the following manner. The intensity value of an X-ray image is proportional to the distance the ray travels through an absorption medium. In an angiogram of the carotid arteries, the absorption medium is the lumen of the carotid arteries filled with radiopaque substances. As an X-rays travels through the absorption medium, X-rays are absorbed, and X-ray intensity decreases. Therefore, at the points where the carotid arteries are thicker, the lumen area filled with radiopaque substance is larger, resulting in a darker (more intense) X-ray image—the X-rays must make their way through larger amounts of absorption medium and greater attenuation occurs. At the points where the carotid arteries are thinner, the lumen area filled with radiopaque substance is smaller, resulting in a lighter (less intense) X-ray—the X-rays make their way through smaller amounts of absorption medium and less attenuation occurs.

BRIEF DESCRIPTION OF THE DRAWINGS

FIG. 3(*b*) is a flow chart of the steps shown in FIGS. 4(*a*)–4(*i*).

FIG. 7 shows an X-ray traveling through an artery from b to point a.

FIG. 13 includes Table 1 that compares the areas of a computer generated model and the reconstructed cross-sectional area of a C-shaped artery, using the computer program.

FIG. 14 includes Table 2 that compares the areas of a computer generated model and the reconstructed cross-sectional area of a bifurcated artery, using the computer program.

DETAILED DESCRIPTION OF THE INVENTION

Figure 2:
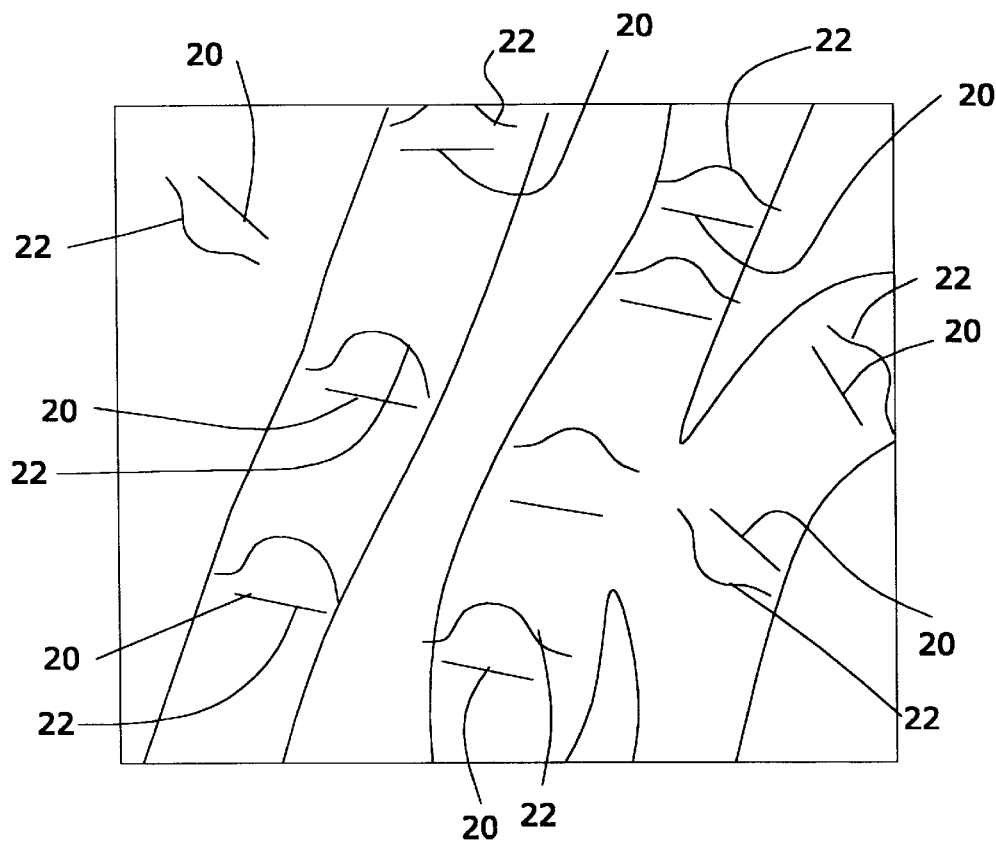
FIG. 2 is an X-ray image of the carotid arteries and shows the intensity lumen function over a real X-ray image.

FIG. 2 illustrates how X-ray intensity value vary across artery sections. FIG. 2 shows intensity lumen function over an X-ray image. By the "intensity lumen function" it is meant variations in the intensity of the X-ray image as a function of the size of the lumen of the carotid arteries. The "lumen functions" are the white curves 12 over the white straight baselines 10 that appear over the dark images of the arteries. The lumen functions are highest toward the center of the lumen. The height of the curve of the lumen function 12 is proportional to the darkness of the image, which itself corresponds to X-ray intensity. To date, this information has utilized.

Our invention not only makes use of the differences in X-ray intensity of the artery image in a single angiogram to determine artery thickness, but we use more than one angiographic image as well. We overcome the problem of trying to determine the three dimensional artery shape by integrating all (or at least more than one) of the X-ray projections available, instead of just using a single two-dimensional view from a single X-ray, as done in the prior art. Using the X-ray projections and the depth information that is provided by all of the angiograms, a "three-dimensional artery model" is created. This allows one to interpret the shape of the carotid arteries more accurately as compared to past devices.

There are two basic steps to our invention:
1. First, an image is acquired using angiographic equipment so that depth information is obtained.
2. Second, the data collected from the angiographic equipment is input into computer with a computer program that determines the three-dimensional shape of the carotid arteries based on the collected data.

Our invention includes a computer program that integrates different X-ray projections (typically four) and reconstructs the artery three-dimensional model. (By "computer" we mean any device that receives and processes data and that performs at least some operations without human intervention. By "computer program" we mean a set of instructions of any nature or manner, that direct the computer to process data in a given manner.) Using computer graphics techniques to be discussed in further detail below, one can display the three-dimensional model and perform anatomical analysis to accurately evaluate the extent of artery stenosis. In such a manner, the computer and computer program is then used to analyze the data and interpret the three-dimensional shape of the carotid artery subjected to stenosis.

A densitometer is used to measure the intensity variation of the X-ray image to determine the thickness of the artery at various points. A densitometer is a device that uses a photoelectric cell (a device that generates electrical energy from light) to detect differences in the density of light transmitted through X-ray film. Because the densitometer can determine the intensity of the X-ray, and X-ray intensity is proportional to the distance the ray travels through the absorption medium, the densitometer may be used to determine the distance the X-ray traveled through the absorption medium. As described, this provides information about the thickness of the artery.

A certain amount of X-ray absorption will be caused by human tissue and other materials apart from the radiopaque material located in the lumen of the artery. This absorption by materials other than the radiopaque injected material is known as the "background" profile. The effect of the background profile needs to be canceled so that measurements of the thickness based on the absorption of X-rays are not distorted. Also, one must take into account the transfer functions of the angiographic material. The transfer function is a measure of mathematical relationship of the output of the system compared to the input of a system. It measures how the system processes a signal as it transported or transferred from input to output. For a discussion on how the cross-sectional area corresponds to the area of the absorption profile, see D. Delacre, C. Smets, P. Suetens, and G. Maxchal, "Knowledge-Based System for the Three-Dimensional Reconstruction of Blood Vessels from Two Angiographic Projections" Med. and Biol. Eng. and Comput., 29:NS27 NS36, November 1991 (this material is hereby incorporated by reference).

Acquiring the Image and Creating the Illumination model

Our invention utilizes two or more X-ray images of carotid arteries. The X-ray images represent selective-catheter angiograms recorded with a digital system. The angiographic equipment is said to be "biplanar" because the artery to be studied is placed substantially on one plane and the angiographic equipment rotates on a plane that is substantially perpendicular to the plane the arm is on. As can be seen in FIG. 3, the arm of the angiographic equipment rotates on a plane allowing images to be taken from different angles. The biplanar equipment simultaneously takes at least two sets of images, each set of images consisting of two individual images that are 90° apart, so that the total number of images equals at least 4. Typically, two shots 45° apart are taken, resulting in four equidistant angiograms: −45°, 0°, 45°, and 90° (or equivalently, 0°, 45°, 90°, and 135°). Such equipment is conventional.

FIG. 3 shows a representation of the adopted coordinate system of biplanar angiographic equipment. Note the x, y and z coordinates. The angiographic equipment rotates about the y axis along the circle demarcated by the points −45°, 0°, 45°, and 90°. This assures that all the X-ray images are taken about the same vertical y axis. The angle represents the actual camera angle, and the densitometer scanning takes place from left to right (or vice versa). The camera angle is actually at 90° to the angle of scanning. As seen in FIG. 3a, at 0° the camera images the artery along the x-axis densitometer. (This will be shown in further detail below in the discussion of FIG. 4.) The equipment arm upon which the patient is laid rotates on a plane parallel to the x-z plane.

The patient is laid on a table so that the artery of interest is approximately at the center of the arm rotation of the angiographic equipment. It can be assumed that the artery of interest will stay at the center of the arm of rotation. It also can be assumed that all the X-ray images are all taken with the same focal distance. (The focal distance is the distance from the point of focus to the lens of the X-ray equipment). Knowledge about the distance of the arm center of rotation is also needed to reconstruct the three-dimensional model to its true scale.

Each angiogram is taken in two steps. First, an X-ray image of the artery is taken. This first image is taken before anything is injected into the body and represents the normal condition. This X-ray is known as the "background image." The background information is used to determine the amount of absorption of X-rays which is not attributable to the injection of a radio-opaque substance. Thus, when radiopaque material is added, the amount of absorption not attributable to that radiopaque material is known and can be corrected for using the background information. Second, radio-opaque dye is injected through the use of a catheter threaded inside the patient's arterial system, after which a second X-ray image is taken. This second image is known as the "foreground image." The combination of both the background and foreground images allows for the identification of the luminal silhouette (silhouette image of the lumen of the artery) and provides depth information about the thickness of the arteries. A computer then subtracts the background image from the foreground image to render an unobstructed view of the arteries. This technique is often referred to as "Digital Subtraction Angiography."

X-ray imaging can be simulated through an illumination model known as "attenuation projection" where only the absorption of the medium is modeled. By "illumination model" it is meant a model of X-ray intensity that can be constructed based on the amount of X-ray absorption. The attenuation projection is a prediction of the amount of attenuation of an X-ray beam due to the absorption of the injected radiopaque contrast medium that was injected in the lumens of the carotid arteries. The attenuation projection is based upon certain known values. For a discussion of creating an illumination model where only the absorption medium is modeled, see K. L. Novins. Towards Accurate and Efficient Volume Rendering. PhD thesis, Program of Computer Graphics, Cornell University, 1994 (this material is hereby incorporated by reference).

Figure 7:
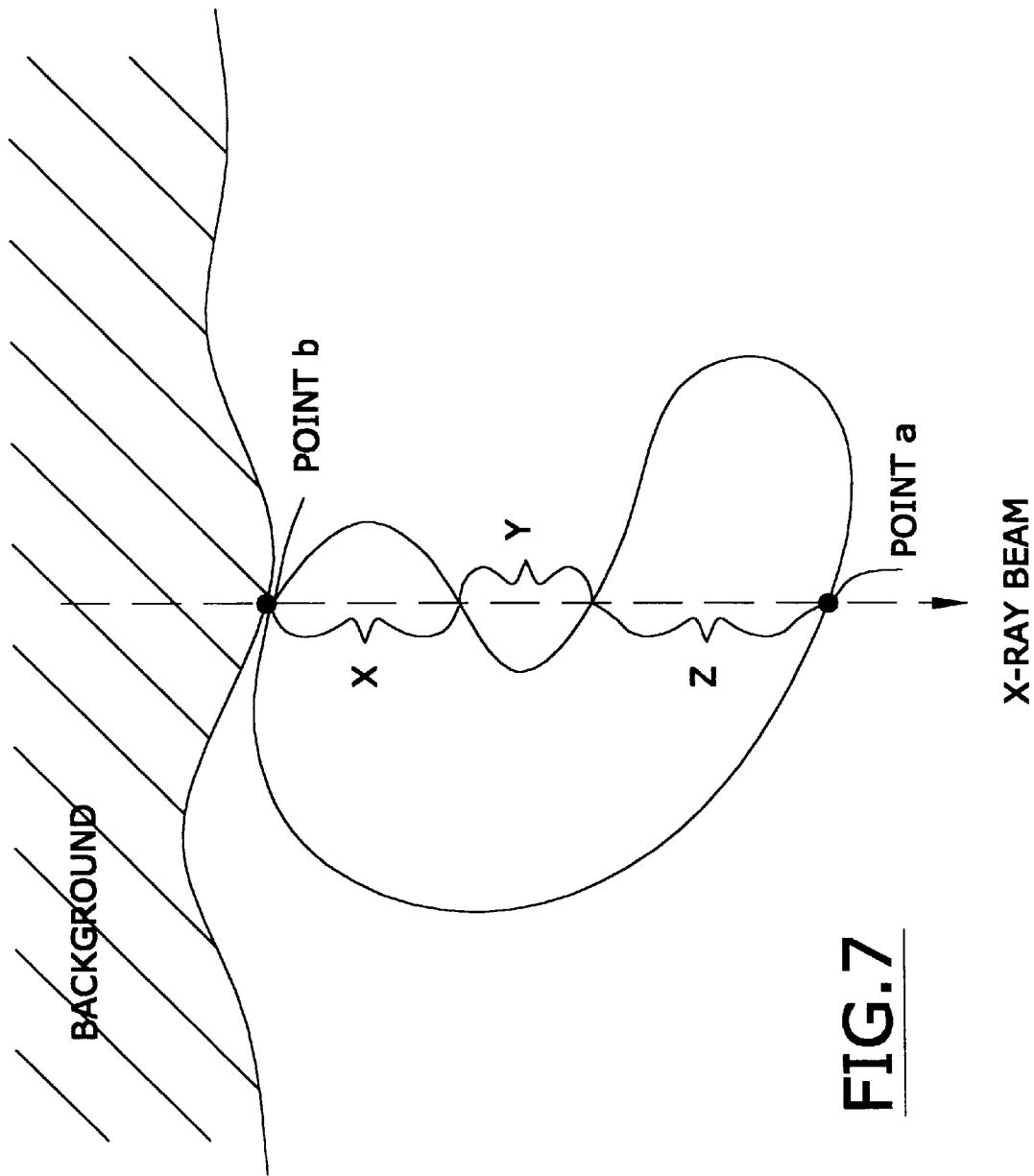

With reference to FIG. 7, assume an X-ray beam travels from point b to point a passing through a medium that absorbs X-rays. Further suppose the intensity of the X-ray beam at point b is known and is denoted $I_b$. Also assume that the coefficient of absorption, $\alpha(v)$, of the material that the X-ray will have to travel through is known. $\alpha(v)$ represents the coefficient of absorption, which determines the fraction of X-rays that are absorbed by the medium along a particular line segment. The intensity of the X-ray image at point a, denoted by $I_a$, after it passes through an absorptive material beginning from point b may be projected (predicted) knowing the intensity at point b ($I_b$) and the coefficient of absorption. The attenuation projection, not considering scattering effects, states that the amount of X-rays that reaches point a, knowing the intensity of the X-rays at point b and the coefficient of absorption of the medium that the X-rays must pass, is given by the relationship:

Attenuation Projection: $I_a = I_b e^x$, where $X = \int_a^b -\alpha(v) \, dv$.

Thus, if one knows the intensity of light at point b ($I_b$) and knows the coefficient of absorption ($\alpha(v)$), one can determine the intensity of the light at point a ($I_a$) using the formula given above.

It is important to note that the attenuation projection from point a to point b only projects the total amount of absorption of the X-ray beam by the medium along the path from a to b. There may be some points along the path from a to b that is very absorptive. There may be other points that are much less absorptive. The attenuation projection provides no information as to what parts are more absorptive and what parts are less absorptive. The order in which the material is encountered as the X-ray passes through the medium is irrelevant to the attenuation projection calculation. As seen FIG. 7, the X-ray travels from b to point a of SO passing through segments X, Y and Z. If the lumen were filled with a radiopaque dye, there would be much more absorption in segments X and Z as compared to segment Y, which may consist of normal human tissue or plaque. However, the attenuation projection would only calculate the total attenuation along the points from b to a, and could not make determinations as to the amount of absorption attributable to segments X, Y, and Z individually.

Because we are interested in knowing the amount of light absorbed by the injected dye, we may say that the background images represent the intensity at point b and the foreground image represents the corresponding point a. Thus, looking at FIG. 7, point b would represent the intensity of an X-ray due absorption of the background. Point b of FIG. 7 would represent the intensity at the foreground. We can now determine the amount of absorption between points a and point b since we now know the amount of absorption attributable to the background. Assuming the dye is homogeneously distributed across an artery section, the coefficient of absorption becomes a constant, and we can rework the above equation yielding:

$$d = -1/\alpha \log(Ia/Ib)$$

Figure 8:
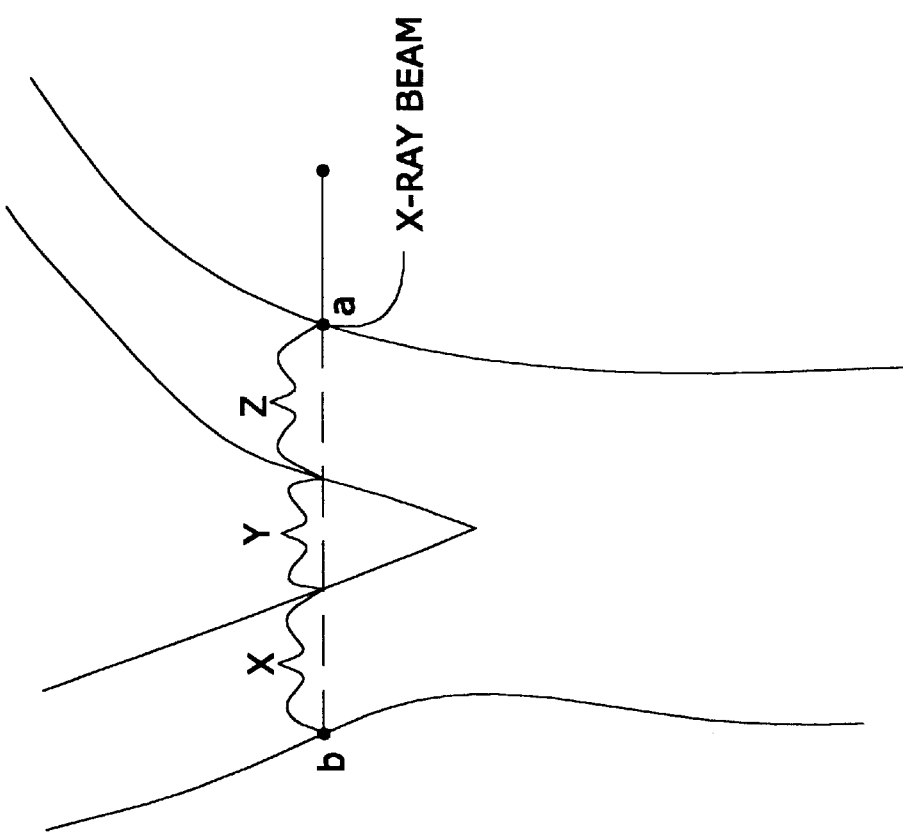
FIG. 8 shows an X-ray traveling different arteries from different branches.

Here, d represents the distance the ray travels through the artery. It is important to keep in mind that such a distance that the ray travels may not be continuous, as can be seen in FIG. 7. That is, the ray may pass through different parts of a same artery section that is concave. As seen in FIG. 7, the ray passes through segment Y, which is outside of the artery. In FIG. 7, the distance through the artery would be segments X+Z. Also, the distance may not be continuous in that the ray may pass through different arteries from different branches (notably near artery bifurcation), as seen in FIG. 8. In FIG. 8, that distance would be X+Z. Again, as seen in FIG. 8, section Y would contribute to the distance d. The formula for determining the distance the ray travels (d) will provide us with a unique distance value representing the sum of all distances the ray travels through the arteries filled with the contrast dye.

Figure 9B:
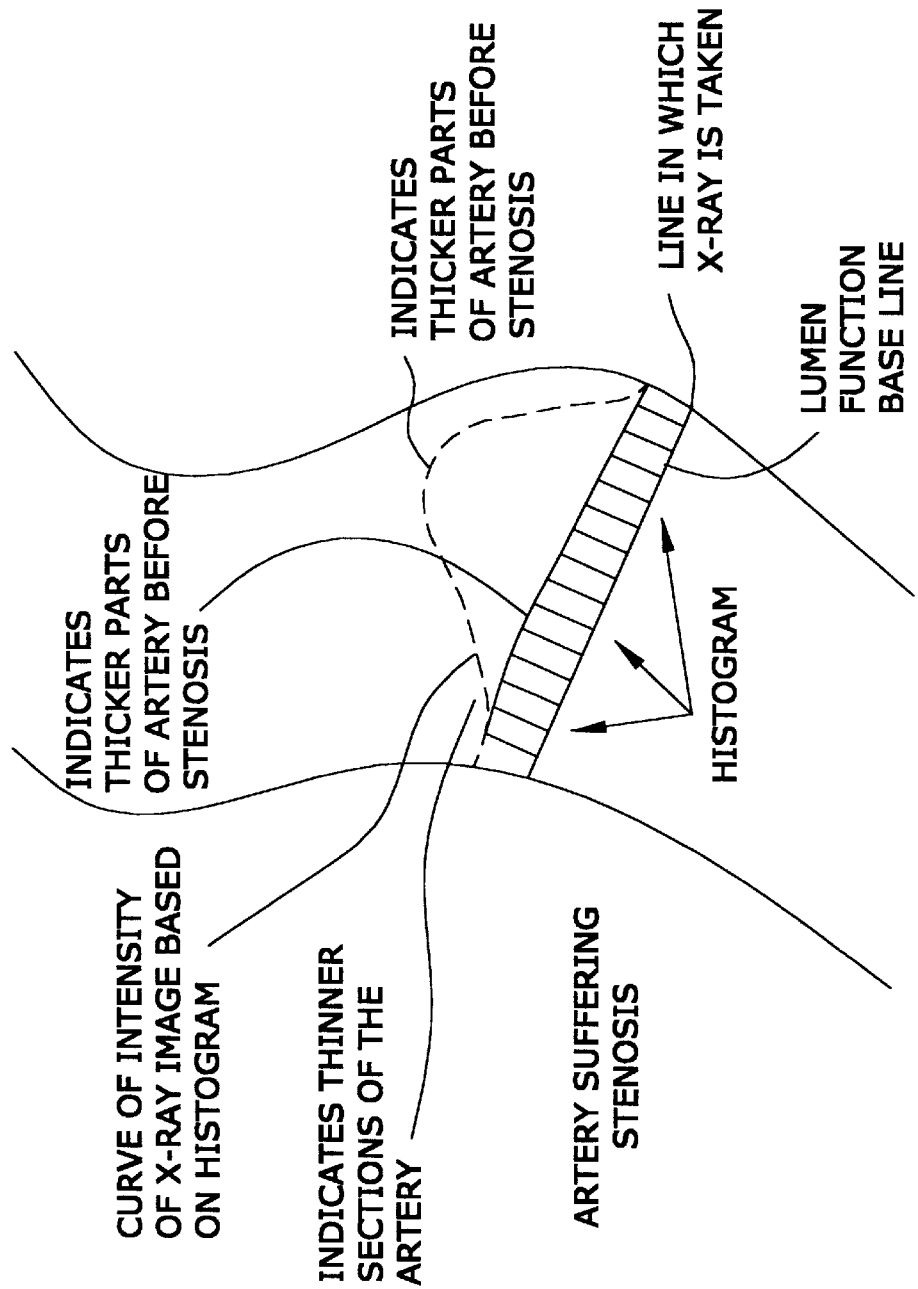
FIGS. 9(*a*) and 9(*b*) show a blowup of one of the arteries where a line is drawn across the arteries in which the X-ray is taken and the lumen function is shown.

From both background and foreground images we can extract a function along any line on the angiographic images that reports the sum of all the distances, up to a scale factor, traveled by the ray through the arteries. FIG. 2 illustrates such functions which we call "lumen functions" and which are numbered 12. FIG. 9a shows a blowup of one of the arteries prior to the onset of carotid artery stenosis. FIG. 9b shows a blowup of one of the arteries prior to the onset after, whereby a curve of the lumen functions before the onset of stenosis, is shown with a dotted line.

Ultimately, the height of the curve corresponds to the thickness of the artery section. FIG. 2 shows these curves along particular lines of the carotid arteries. The curved line is a function of the thickness of the artery and the luminal area. We call the curved line "lumen functions." As previously noted, a lumen function may be defined as the resulting curve indicating lumen depth (artery thickness) that is based on information obtained from X-ray intensity. These lumen functions may be "reconstructed" by gathering data at other angles and realigning the curve so that it more accurately reflects the true shape of the carotid arteries. The reconstruction computer program we present is based on these lumen functions. In actual practice, the value of the coefficient of absorption is usually unknown, although constant across arteries' cross-sections.

Using the Lumen Function to Construct the Artery Images

As discussed, our invention combines different X-ray projections to reconstruct the three-dimensional artery model. The image of the carotid artery is based on biplanar selective-catheter angiograms. (The term "biplanar" will be defined below.) The integration of more than one projection is based on the assumption that the artery movement is negligible. This assumption is reliable because carotid artery lesions usually occur near the artery bifurcation. The bifurcation of the carotid arteries and the plaque formation adds stiffness to the artery structure, minimizing artery movement. Indeed, motion artifacts have been noticed not to affect the measurement of the area of stenosis. (An "artifact" is a component of a signal that is extraneous to the variable represented by the signal. In the present application, a "motion artifact" is an extraneous signal that is a result of the patient's motion.) See J. Link, S. Mueller-Huelsbeck, J. Brossmann, M. Grabener, U. Stock, and M. Heller, "Prospective Assessment of Carotid Bifurcation Disease with Spiral Ct Angiography in Surface Shaded Display (S)-technique." *Computerized Medical Imaging and Graphics*, 19(6):451–456 (1995) (this material is hereby incorporated by reference).

An artery reconstruction, may be done using different image techniques such as computerized tomography (CT) angiograms, intravascular ultrasound, transcutaneous ultrasound, and magnetic resonance imaging (MBI). In general, despite the image technique applied, all artery reconstruction computer programs face common challenges. The first one is related to image feature detection, for instance, how to detect the artery boundary on an image with minimum, if at all necessary, user intervention. Several computer techniques can be used to perform such a task, including a pure geometric approach, a physically-based approach, and thresholding techniques.

A "thresholding technique" is an image-processing technique (a technique for highlighting or suppressing certain features in an image)in which the points of an image at or near a certain point are highlighted. In a gray-scale image, such as that produced by X-ray imaging, this highlighting can be done by converting all pixels below some value to black, and all pixels above that value to white, producing a threshold edge between the black and white images. With "thresholding," the grayscale values of the pixels generated by the X-ray are compared to a fixed threshold value. A grayscale refers to series of tones ranging from white to pure black that are often assigned numerical values representing the particular tone. Depending on whether the pixel values are higher or lower than the threshold, the output line pixel is saved as either black or white.

For an understanding of the pure geometric approach, see, O. Faugeras, "Three-Dimensional Computer Vision: A Geometric Viewpoint" The MIT Press, Cambridge (1993) (this material is hereby incorporated by reference). For an understanding of the physically-based approach, see, M. Kass, A. Witkin, and D. Terzopoulos, "Snakes: Active Contour Models," *International Journal of Computer Vision*, pages 321–331, 1988 (this material is hereby incorporated by reference). See also, Rafael C. Gonzalez and Paul Wintz, *Digital Image Processing*, Addison-Wesley, Reading ($2^{nd}$ ed.) (1987) (this material is hereby incorporated by reference). For an understanding of thresholding techniques, see P. K. Sahoo, S. Soltani, and A. K. C. Wong, a Survey of Thresholding Techniques, Computer Vision, Graphics, and Image Processing 41:233–260 (1988) (this material is hereby incorporated by reference). See also, Rafael C. Gonzalez and Paul Wintz, *Digital Image Processing*, Addison-Wesley, Reading, second edition (1987)(this material is hereby incorporated by reference). The X-ray images of angiograms are usually of such a high quality that the pure geometric approach, a physically-based approach, and thresholding techniques will suffice to detect images with a minimal amount of user intervention. We have achieved best results using a thresholding technique initially presented by Chow and Kaneko and described by Gonzalez and Wintz. See above. The X-ray image of the carotid arteries is subdivided in several overlapping images. Then we compute the histogram of each subimage and fit it to an analytical Gaussian distribution (bell-shaped curve). For an understanding of how to compute the histograms of each subimage, see [D. M. Titterington, A. F. M. Smith, and U. E. Makov, *Statistical Analysis of Finite Mixture Distributions*. John Wiley & Sons, Chichester (1985) (this material is hereby incorporated by reference). See also, M. Aitkin and G. T. Wilson, "Mixture Models, Outliers, and the Em Computer Program" Technometrics, 22(3):325–331, August 1980 (this material is hereby incorporated by reference).

If a bimodal distribution is found of the intensity of the X-ray images for a subimage, we can compute an optimal threshold for that subimage. A bimodal distribution is statistical term meaning that there are two modes. A mode is the most frequent occurring number of a set of numbers. Bimodal means having two modes in a distribution. A bimodal distribution is a probability distribution with two different values that appear more frequently than neighboring values. Threshold values to segment the entire image are obtained by interpolating and averaging subimage values.

Figure 5C:
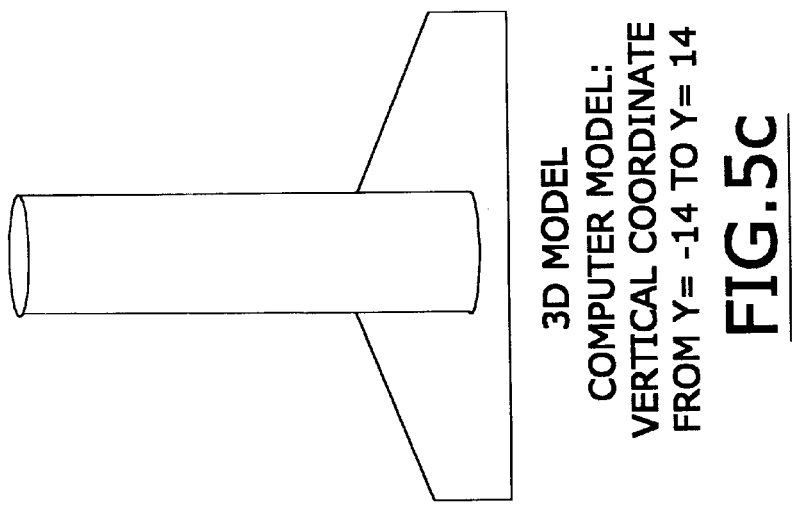
FIGS. 5(*a*) to 5(*i*) show the generation of a three dimensional image of the carotid arteries created by interpolating the cross-sections of the artery.
Figure 5B:
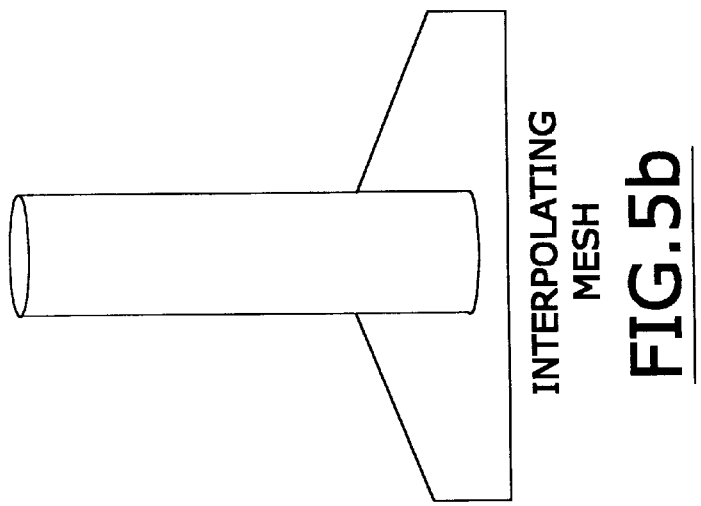

Since the different X-ray projections share a same vertical y axis (see FIG. 3b), we reconstruct a set of cross-sections parallel to the x-z plane and then interpolate these cross-sections to obtain the three-dimensional luminal surface. This process can be seen in FIGS. 5(a), (b) and (c). In FIG. 5(b), the cross-sections of an artery are determined just above each other. After that, a three-dimensional model is created as seen FIG. 5(b) and FIG. 5(c). In that manner, if the artery three-dimensional orientation is required, it is extracted after the generation of an image of the surface of the arteries. After the four images are taken, each image is scanned through a densitometer. Scans along the same plane in each of the four images are compared together to reconstruct a 30 graphic image of the artery.

The Reconstruction Computer Program

Figure 12:
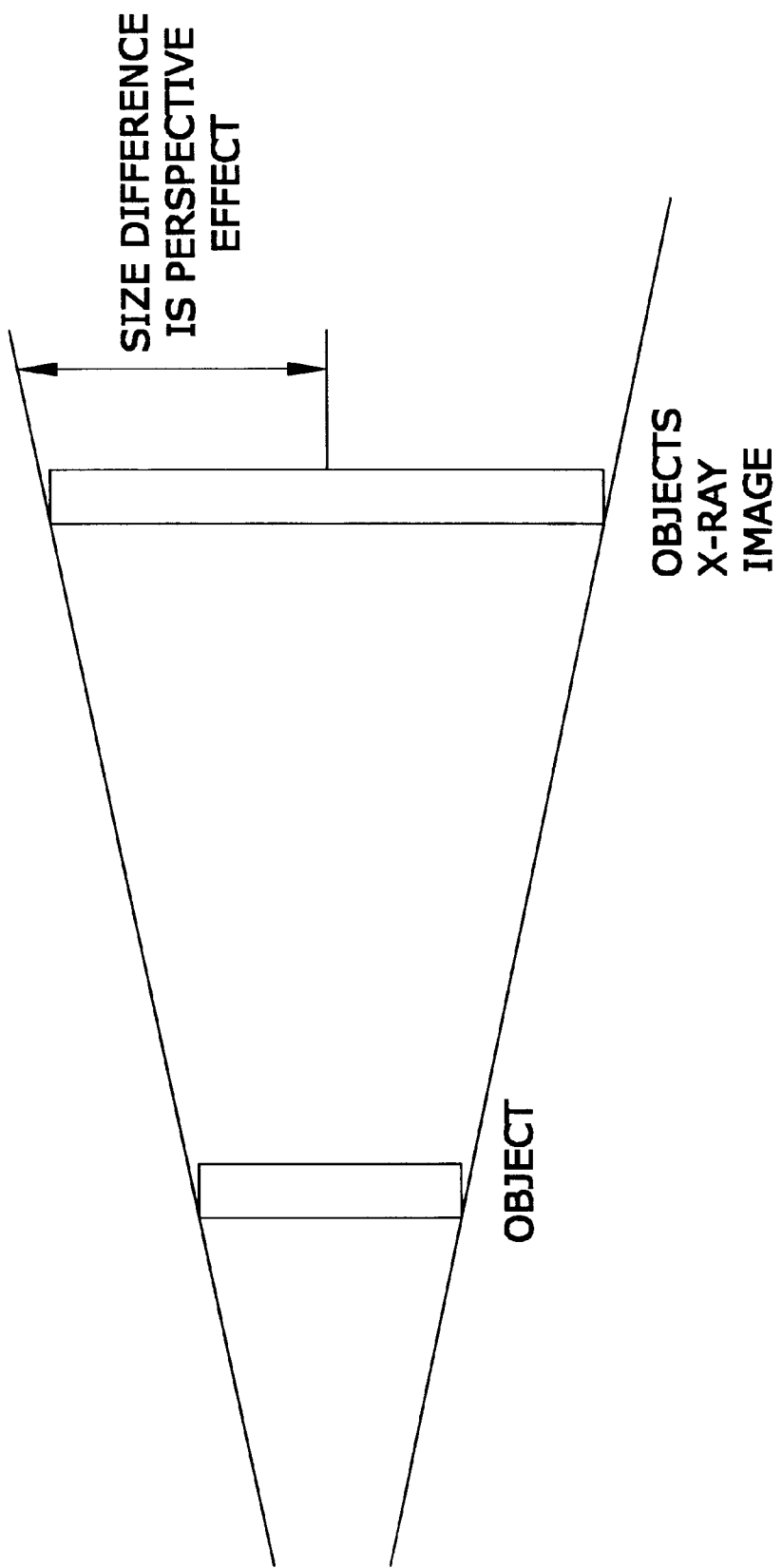
FIG. 12 shows the perspective effects of an X-ray image.

Using existing densitometer and computer graphic technology, our invention reconstructs a graphic image of the artery using a heuristic approach that is capable of handling artery cross-sections with relatively complex shapes, including overlapping side branches or disease at artery bifurcation. A "heuristic approach" is a method of solving a problem in which one tries each of several approaches and evaluates progress toward a solution after each attempt. The perspective effects (distortions of relative sizes due to the fact X-ray beams are emitted at an angle) are insignificant since the "camera" angle of view to. take the X-rays is very small (usually $\leq 7°$) FIG. 12. shows the perspective effects of an X-ray image.

Figure 3B:
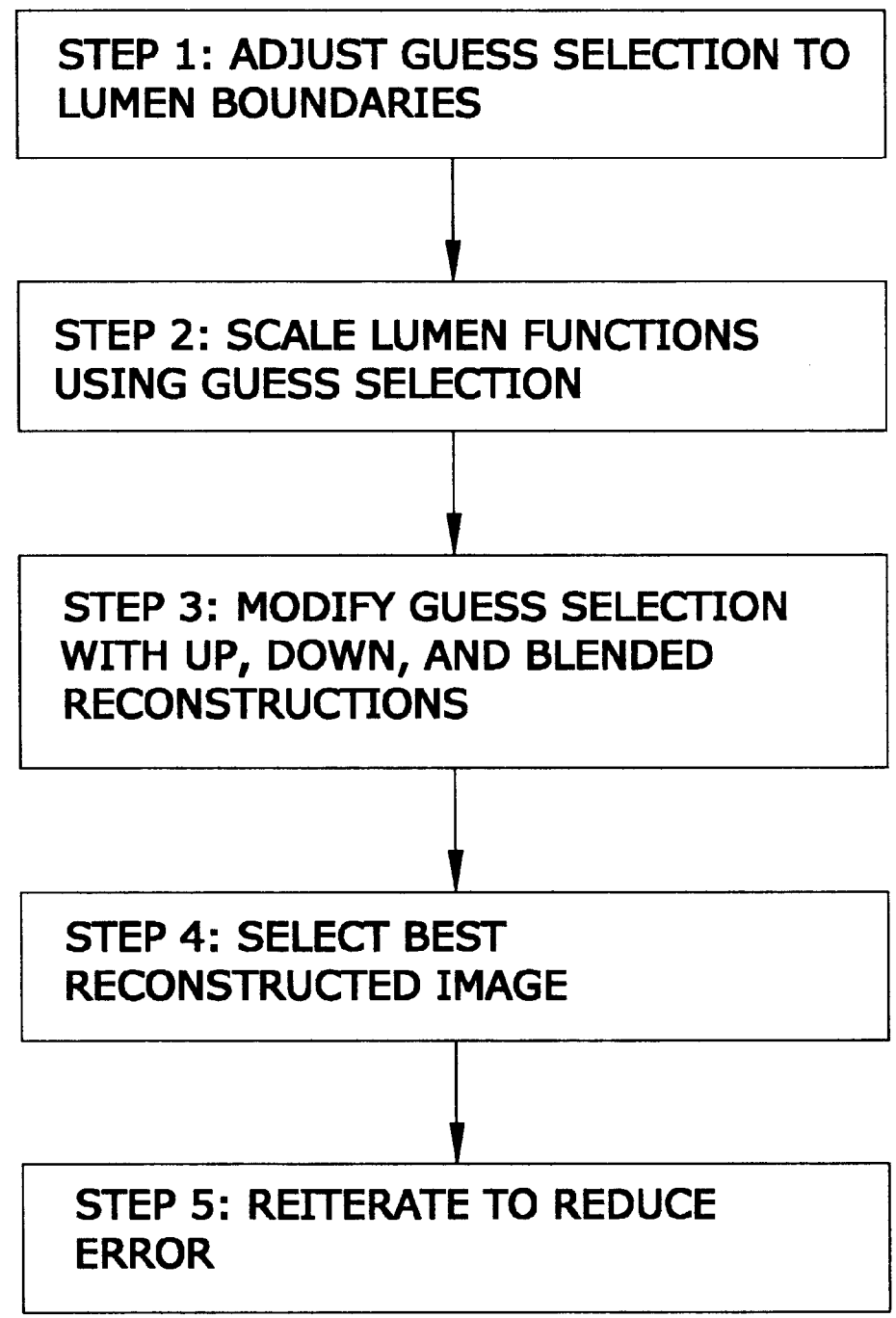
FIG. 3(*a*) is a diagram of an apparatus with the three-dimensional axis orientation to be utilized when using the angiographic equipment.

The reconstruction computer program can be summarized by the following steps as shown in FIG. 3(b) (or pseudo code) that is to be performed on a computer;

Reconstruct cross-section
  in: initial guess section
  out: reconstructed section
    1. Transform initial section to fit lumen boundaries.
    2. Scale lumen functions.
    3. For each lumen function (corresponding to each x-ray projection)
      * Adjust initial section yielding a reconstructed section
    4. Choose the best reconstructed section.
    5. If reconstruction error <previous reconstruction error then
      * Go to first step assuming reconstructed section as initial else
      * Return previous reconstructed section A "heuristic routine" or "heuristic program" is a program in which a computer tries each of several methods of solving a problem and judges whether the program is closer to the solution after each attempt. An initial guess section 26 can be seen in FIG. 4(a) as the object in the center represented by the dotted lines, the dotted lines indicating that the shape is not known. The "initial guess section" is the initial guess as to what the artery probably looks like. After we make are initial guess as to the shape of the artery section, the subsequent sections are called "reconstructed sections" or "reconstructed guess sections" to indicate that the initial guess section has been reconstructed and modified in conformity to the new guess as to what it probably looks like. The guess section 26 in FIGS. 4(c)–4(i) may no longer be called an "initial guess section", just a guess section, since they are guesses after additional evaluation. The computer program is based on a heuristic routine that uses the lumen functions to modify a given initial guess section resulting in a new reconstructed guess section. The reconstructed guess section is the reconstructed image after more information is gathered.

This process of reconstructing the image so as to produce a reconstructed section 26 is repeated a number of times until the true the shape is obtained. For each reconstructed section 26, the computer program simulates its corresponding lumen functions, using the described illumination model, and compares the reconstructed lumen functions to the original ones, yielding a reconstruction error measure. A "reconstruction error" is a measure of the amount of the error there was when attempting to reconstruct the images of the artery. The error measure is not only used to fine tune the reconstruction process, but also as an indicator of how accurate the reconstruction of the artery image was performed. This allows us to discard inaccurately reconstructed sections 26 when generating the final luminal surface.

Figure 4A:
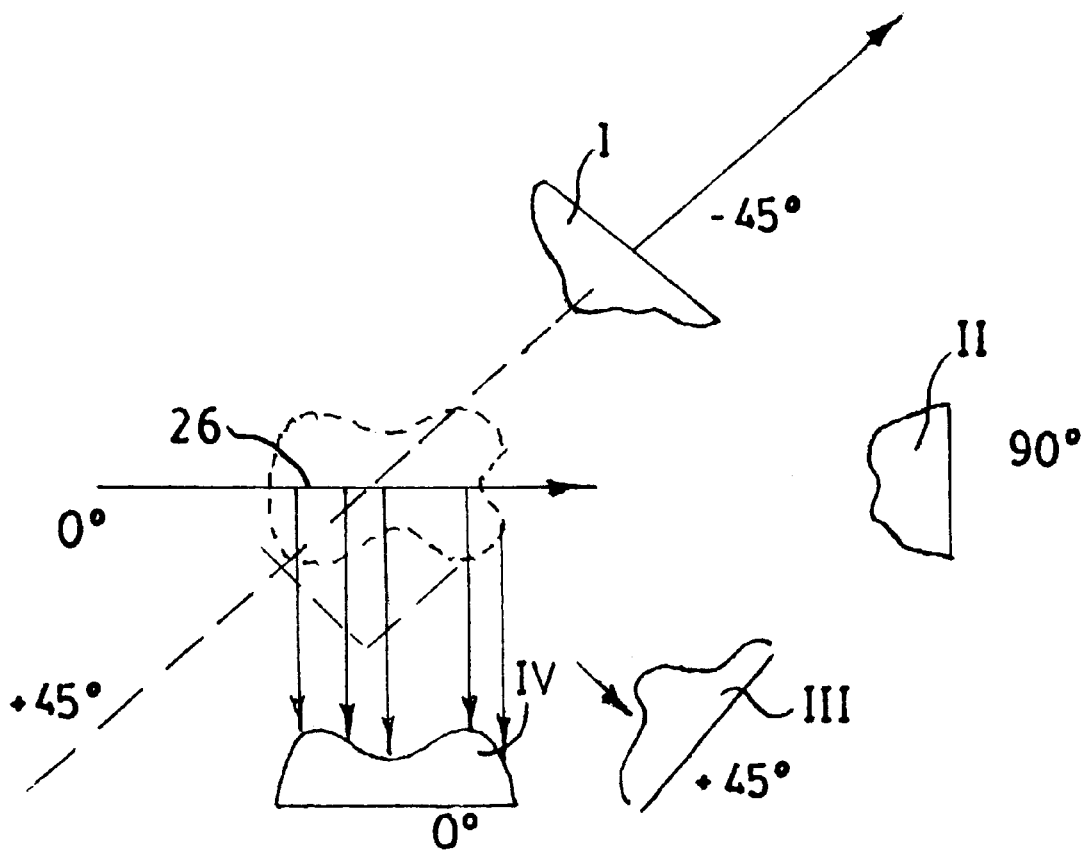
FIGS. 4(*a*)–4(*i*) show an image of a cross-section of a carotid artery being determined using the lumen functions of X-ray images.
Figure 4B:
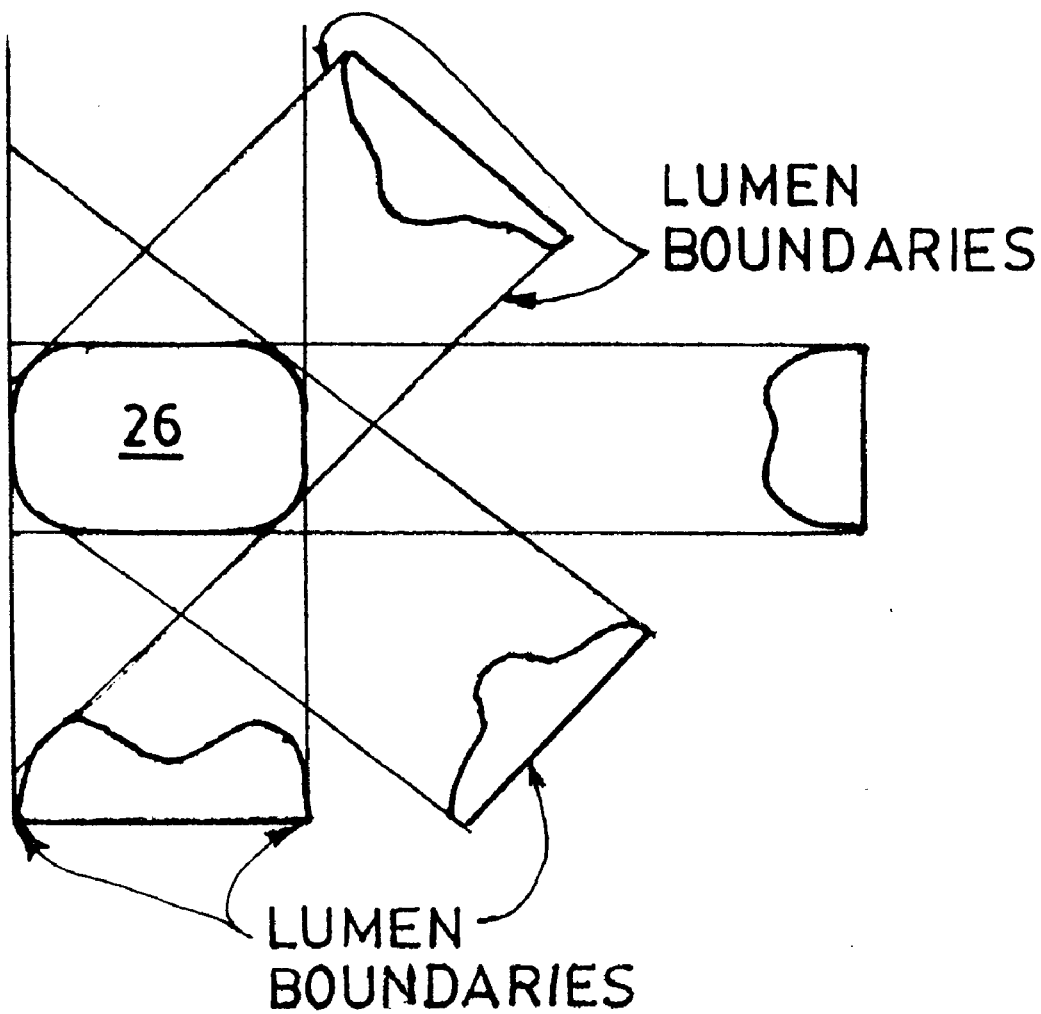
Figure 4C:
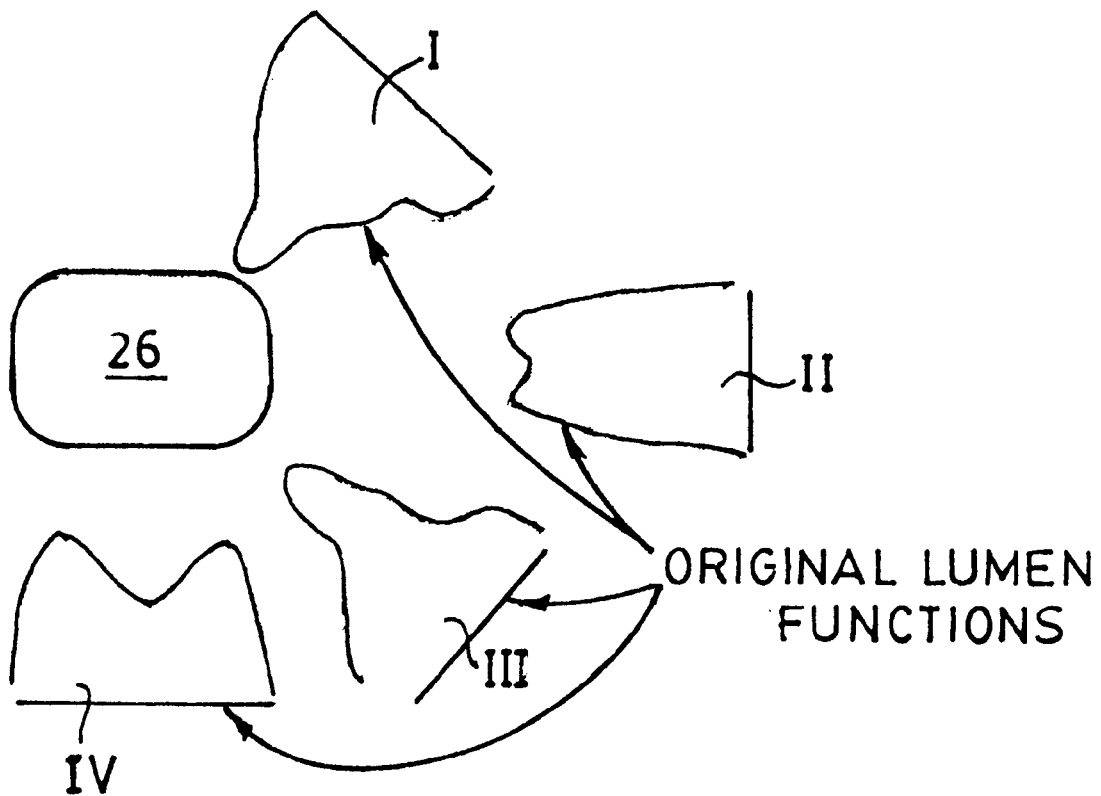
Figure 4D:
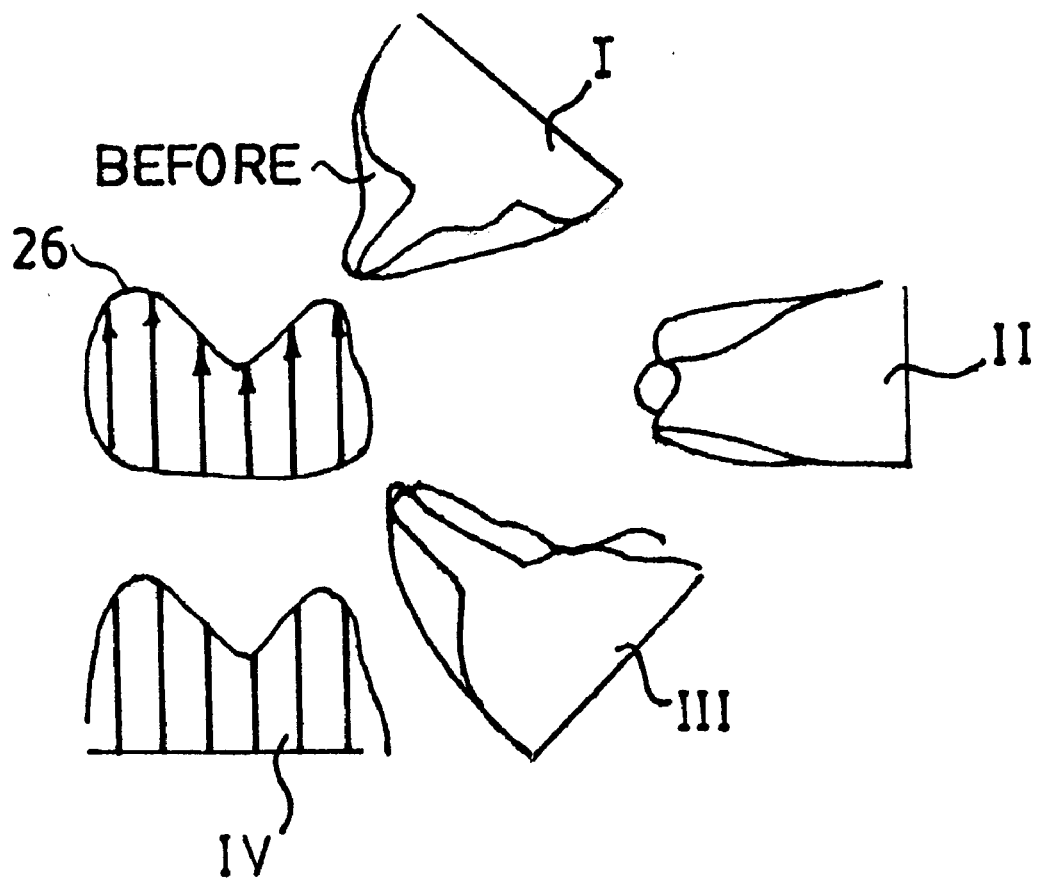
Figure 4E:
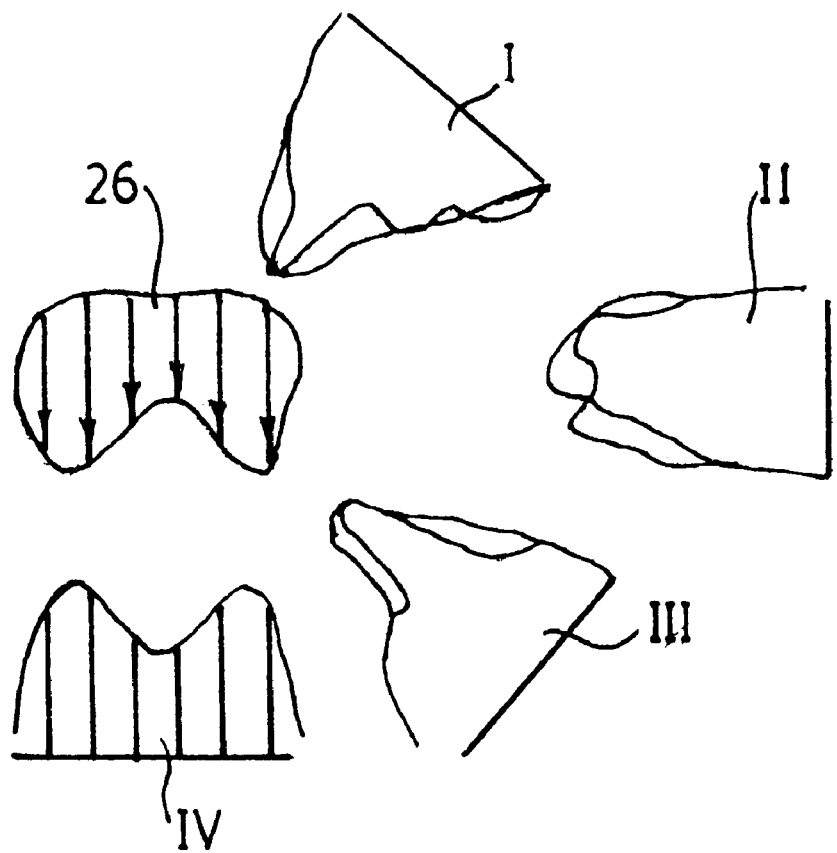
Figure 4F:
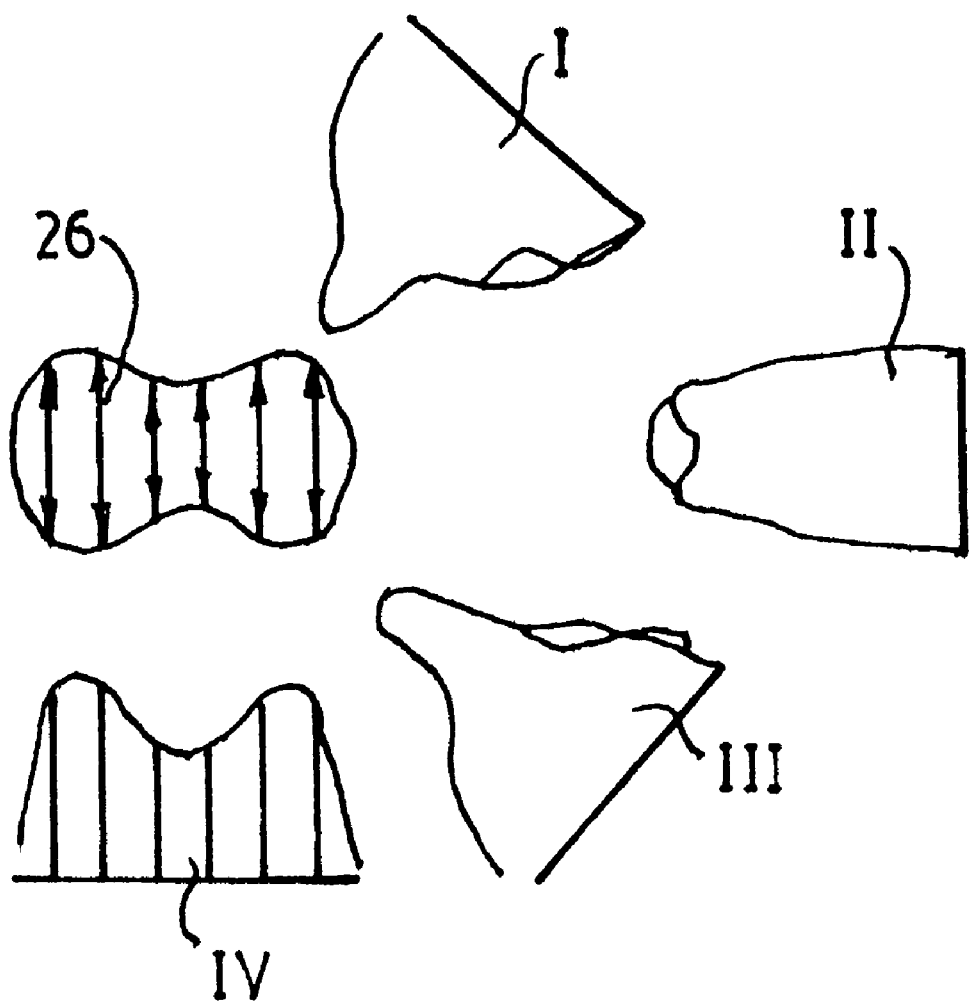
Figure 4G:
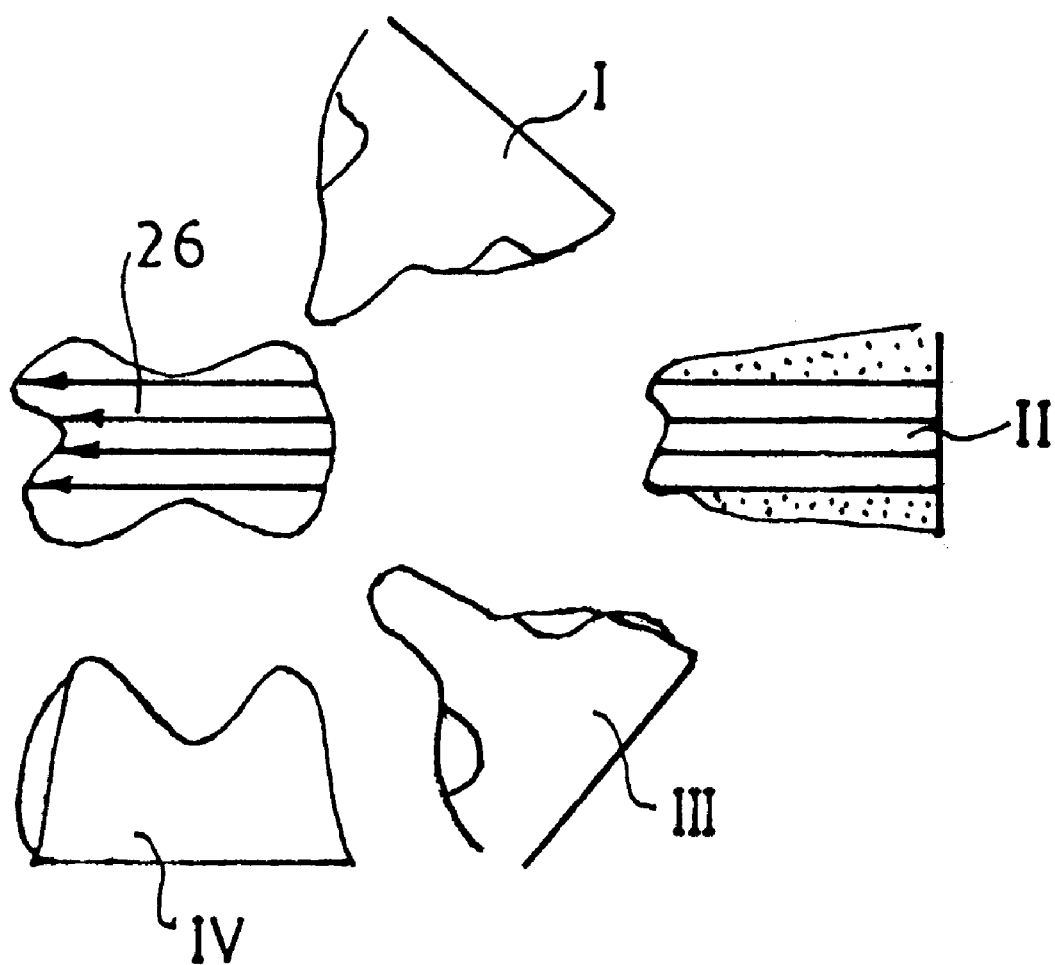
Figure 4H:
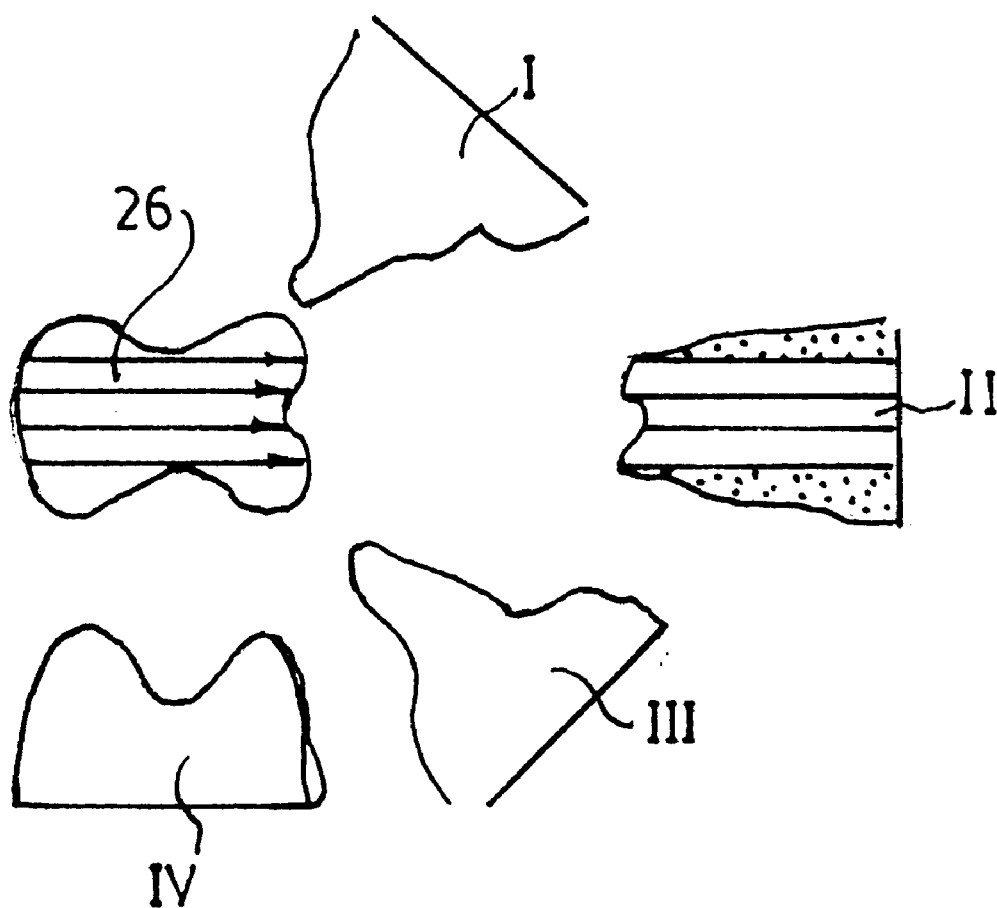
Figure 4I:
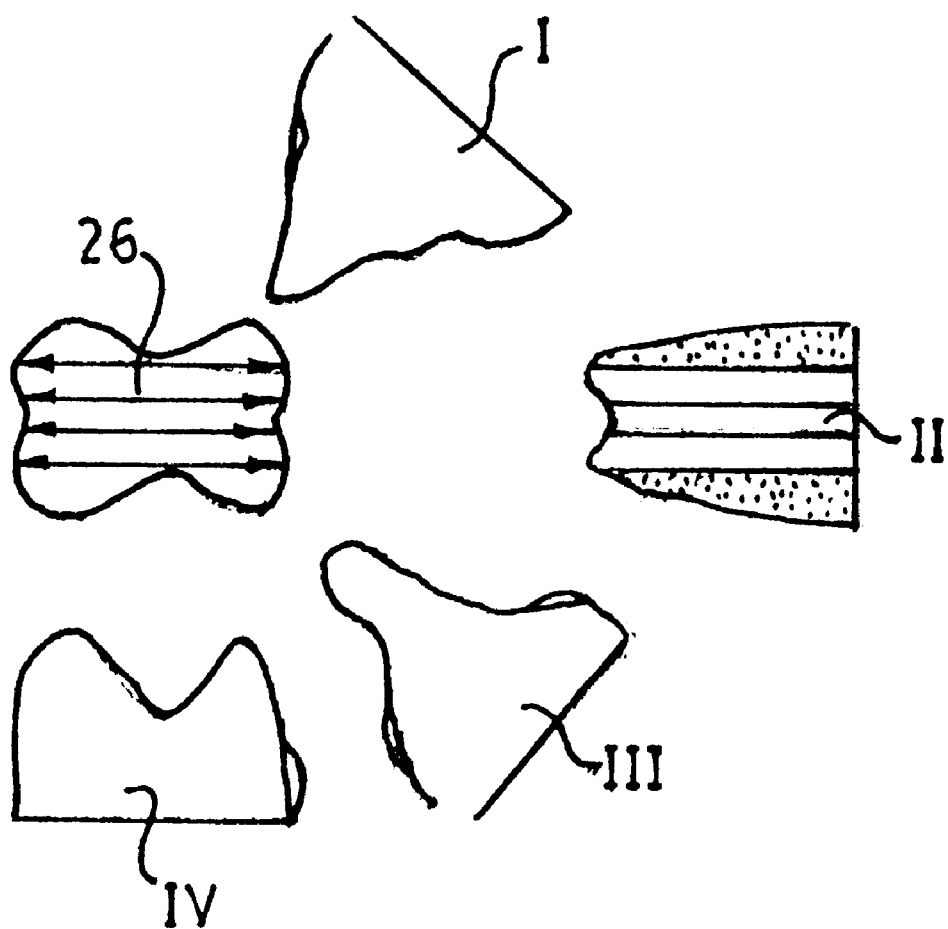

FIG. 4(a)–4(i) illustrates the computer program in action and show how the shape of the carotid artery in a given plane is determined starting from the initial guess section 26. FIG. 4(a) shows the initial guess section 26. FIGS. 4(b)–4(h) show the restructuring of the initial guess-section 26 based on data obtained from the lumen functions and the reconstruction error. FIG. 4(i) shows the finally determined carotid artery shape. This process is set forth in detail below.

FIG. 4(a) shows an initial guess cross section 26 and its respective lumen functions I, II, III, and IV. Such a cross-section is likely to exist when carotid stenosis occurs near the bifurcation. The initial cross-section 26, whose shape is unknown, is reconstructed based on the lumen functions, i.e., the graphs of X-ray intensity. The lumen function I represents the image at −45°, lumen function II represents the image at 90°, lumen function III represents the image at +45°, and lumen function IV represents the image at 0°.

Figure 1:
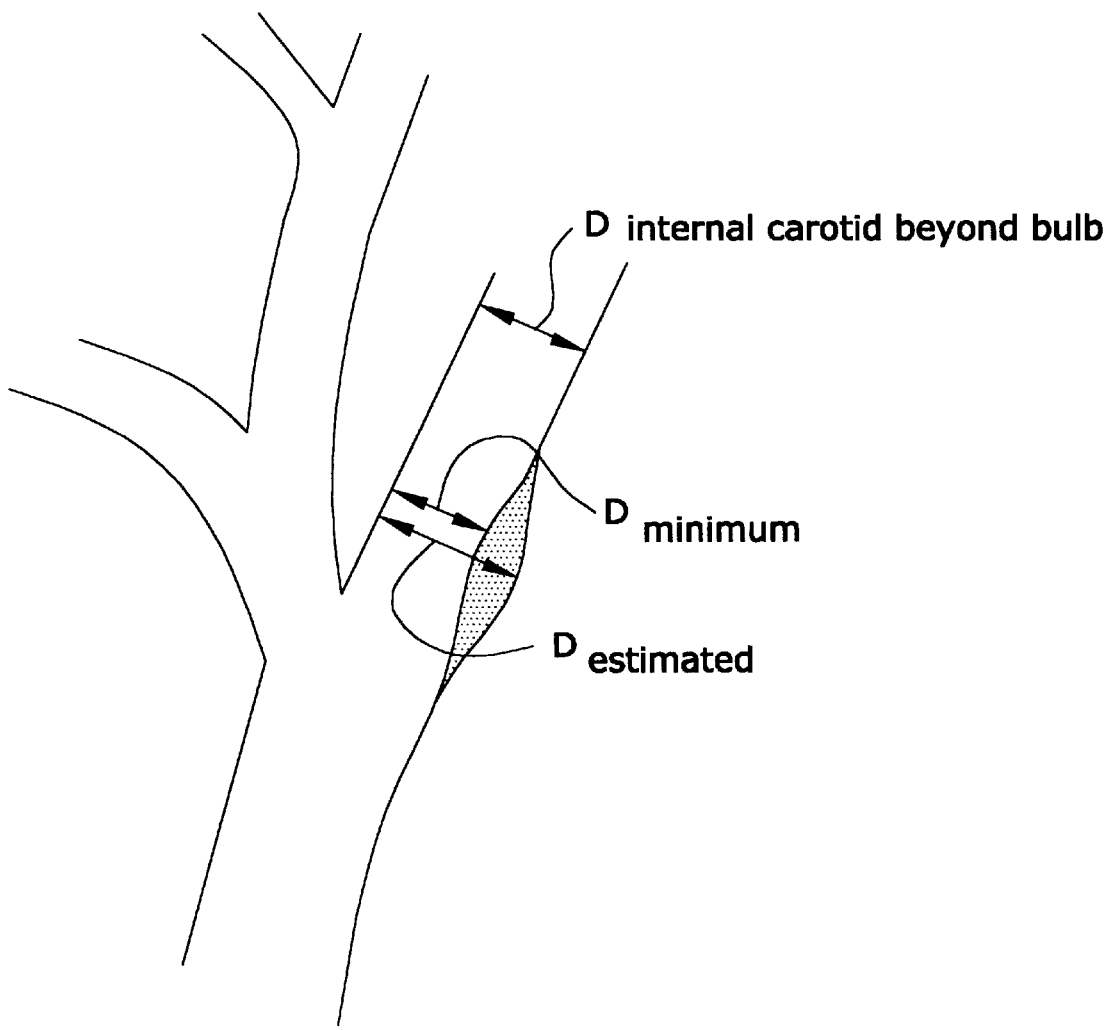
FIG. 1 depicts the carotid arteries and shows various diameters used to determine the extent of stenosis in the Prior Art.

The reader may note that the images −45°, 90°, +45°, and 0° do not align with their usual places on a Cartesian circle. As can be seen in FIG. 4(a), the lumen IV which represents 0° is 90° off from actual 0°. This is because "the lumen function at 0°" means the lumen function of the densitometer readings across an arterial image along a 0° axis. 0° represents the angle of the "camera". So, FIG. 1 is the densitometer histogram of an X-ray image taken at 0° camera angle. As shown with the straight lines in FIG. 4(a), when lumen function IV is being determined, the angiographic equipment is pointed downward. The densitometer scan of the angiogram is from left to right along the 0° axis. Similarly, the X-ray image taken along +45 is represented by a doted line. Similarly, lumen function III, which represents +45, is 90° from true 45°.

The lumen functions are reconstructed as more data are gathered. The corrected (or reconstructed) lumen function will be used to determine the actual shape of the carotid arteries. While the reconstruction of the carotid artery image can take place in as few as one iteration, preferably two or more iterations are used.

The General Steps

The process takes place in the following general manner: First, the lumen functions are scaled as seen by the process in 4(b) resulting in the scaled lumen function as seen in FIG. 4(c). The resulting scaled lumen functions are called the "original lumen functions." These lumen functions will be the object of comparison to later reconstructed lumen functions. The stronger the correspondence between the reconstructed lumen function and the original lumen functions, the better the reconstruction of the lumen function. First, the outline of the guess shape is modified in accordance with lumen function IV. Then, lumen function I, II and III are reconstructed in accordance with lumen function IV. In FIGS., 4(d) and 4(e), an upward and downward reconstruction of the lumen function numbered IV (taken along 0°) is shown. The modified outlines are combined FIG. 4(f), which shows the blending of the upward and downward reconstruction of lumen function IV.

During each reconstruction, the luminal functions I, II, III, and IV are altered to account for the information provided by the reconstructed section 26. The lumen functions I, II, III and IV themselves are reconstructed using the newly reconstructed guess sections 26: the lumen functions I, II, III and IV are changed to account for the new shape of the reconstructed guess section so that the lumen functions I, II, III and IV are long where the artery is deep, and shorter as the artery becomes thinner. These adjusted lumen functions I, II, III and IV are called "reconstructed lumen functions."

A type of feedback process develops. The lumen functions I, II, III and IV are used to reshape the guess section 26, and the reconstructed guess section 26 is later used to reconstruct the lumen functions I, II, III and IV. If the reconstructed lumen functions I, II, III and IV are determined to be favorable reconstructions because they correspond highly with the original lumen functions, the reconstructed guess section 26 is further used in the effort to reconstruct the carotid artery shape. If the reconstructed lumen functions I, II, III and IV are determined to not be favorable reconstructions because they correspond with the original lumen functions is poor, the reconstructed guess section 26 is not longer used in the effort to reconstruct the carotid artery shape.

As can be seen in FIGS. 4(d)–4(i), the reconstructed lumen functions are superimposed over the original lumen functions to determine the "reconstruction error." "Reconstruction error" may be defined as the total combined areas of the original lumen function and the reconstructed lumen function that do not overlap each other. It is a measure of how different the reconstructed lumen function is to the original lumen function. The "best reconstruction" is the one with the least amount of reconstruction error.

Reconstructed lumen functions I, II, III and IV are sought that best match the original lumen functions in shape and size. Thus, the best reconstructed guess section 26 is selected from the upward and downward reconstruction of lumen function IV as seen in FIGS. 4(d) and 4(e), and the blended section 26 as seen in FIG. 4(f), based upon the best reconstructed lumen functions I, II, III, and IV of FIGS. 4(d), 4(e) and 4(f).

This process is reiterated for another lumen function. This second process is called the "second iteration" and is seen in FIGS. 4(g), 4(h), and 4(i). Again, an upward, downward and blended reconstruction is taken, but for the lumen function marked II, instead of the lumen function IV. Again, of these three, the best reconstructed sections 26 is taken from FIGS. 4(g), 4(h), and 4(i) based upon the lumen function with the least amount of reconstruction error.

If the second iteration is better than the first iteration, the algorithm continues, and a third iteration is performed. Otherwise, if the first iteration is better the second iteration, the algorithm stops. If the third iteration is better than the second iteration, the algorithm continues and a fourth iteration takes place. If the third iteration is not better than the second iteration, the algorithm stops and no fourth iteration is performed.

The Computer Program In Detail

Step 1: Transforming the Initial guess Section By Scaling and Translation So as To Fit the Lumen Boundaries The first step of the reconstruction computer program adjusts the initial given section 2 to fit, as far as possible, into the lumen boundaries. The most desired process for determining the initial guess section 26 will be described in further detail below. For now, it is assumed we an initial guess section 26. By "lumen boundaries" it is mean the projected widths of the lumen functions I, II, III and IV as seen in FIG. 4(b). The lumen boundaries are shown by the two perpendicular lines emanating from the ends of the lumen functions I, II, III and IV to the cross-section of the artery. Since the ends of the lumen function indicates both the width and the position of the cross-section, the lumen boundaries may be used to scale the initial guess section according to the carotid artery's approximate true size and position.

To adjust the initial given section 26 into the lumen boundaries, the computer program scales and translates the initial guess section 26. By "scaling" it is meant taking the initial guess section 26 and reconstructing it according to its true size. By "translating" is meant reconstructing the initial guess section 26 so that the initial guess section 26 is moved up or down, left or right, or in and out. Thus the approximate size and position of the artery section is ascertained before its exact shape can be determined through the reconstruction process.

FIG. 4(b) shows the effect of scaling and translating on an initial guess section 26. Note that the initial guess section 26 now has an estimated size and position, but its shape is not now known.

Step 2: Scaling the Lumen Functions Using the Adjusted Initial Guess Section

The second step uses the already adjusted initial guess section 26 (the scaled and translated initial section) to appropriately scale each lumen function I, II, III, and IV. Note the difference in size of the lumen functions I, II, III and IV between FIG. 4(b) when the lumen functions are not scaled, and FIG. 4(c) when they are scaled. An individually scaled lumen function may be seen in FIG. 10. (Remember that the lumen functions depend on an unknown coefficient of absorption.)

For each lumen function a ray is traced, accordingly to the X-ray direction and its point of maximum value. Then the distance traveled by this ray through the initial guess section 26 is computed. The distance traveled by the ray through the initial guess section 26 is the "distance value." Thus the adjusted initial guess section 26 that was fitted into the lumen boundaries of the lumen functions I, II, III and IV are used to rescale the lumen functions themselves. The "maximum lumen value" is the highest point on the curve of the lumen function prior to scaling. See FIG. 10. The ratio of the distance value and the current maximum lumen value represents the scale factor to be applied to the lumen function.

Scale Factor=distance value/maximum lumen value

After scaling each lumen function separately, we compute each lumen function area. The "lumen function area" is the area underneath the lumen function curve which ultimately represent the total cross-sectional area of the lumen. All lumen functions I, II, III and IV should have the same lumen function area since they are measuring the same cross section 26 of the artery only from different angles. The low parts of the curve and the high parts of the curve of the lumen function, which respectively represent the thin parts and thick parts of the artery, may be located along different parts for each individual luminal function I, II, III and IV. But the total area underneath the luminal curve, which represents the total area across a cross section of the artery, must remain constant. However, due to noise effects and inaccuracy of the initial guess section in representing the actual unknown section, the area of a lumen function will likely be different from the others. All lumen functions I, II, III and IV need to be corrected so that the lumen areas are the same. To correct this, we use the median lumen area value to re-scale each lumen function so that they all have the same area. FIG. 4(c) shows the scaled lumen function. The areas of I, II, III, and IV in FIG. 4(c) are the same, the size of the area being equal to the median lumen area of lumen functions I, II, III, and IV prior to scaling.

Having scaled the lumen functions I, II, III, and IV so that they appear as they do in FIG. 4(c), we will use these lumen functions as they are appear in FIG. 4(c) as a point of reference to be compared with reconstructed lumen functions to be generated later. Thus, the lumen functions I, II, III and IV in FIG. 4(c) are considered to be the "original lumen functions."

Figure 10:
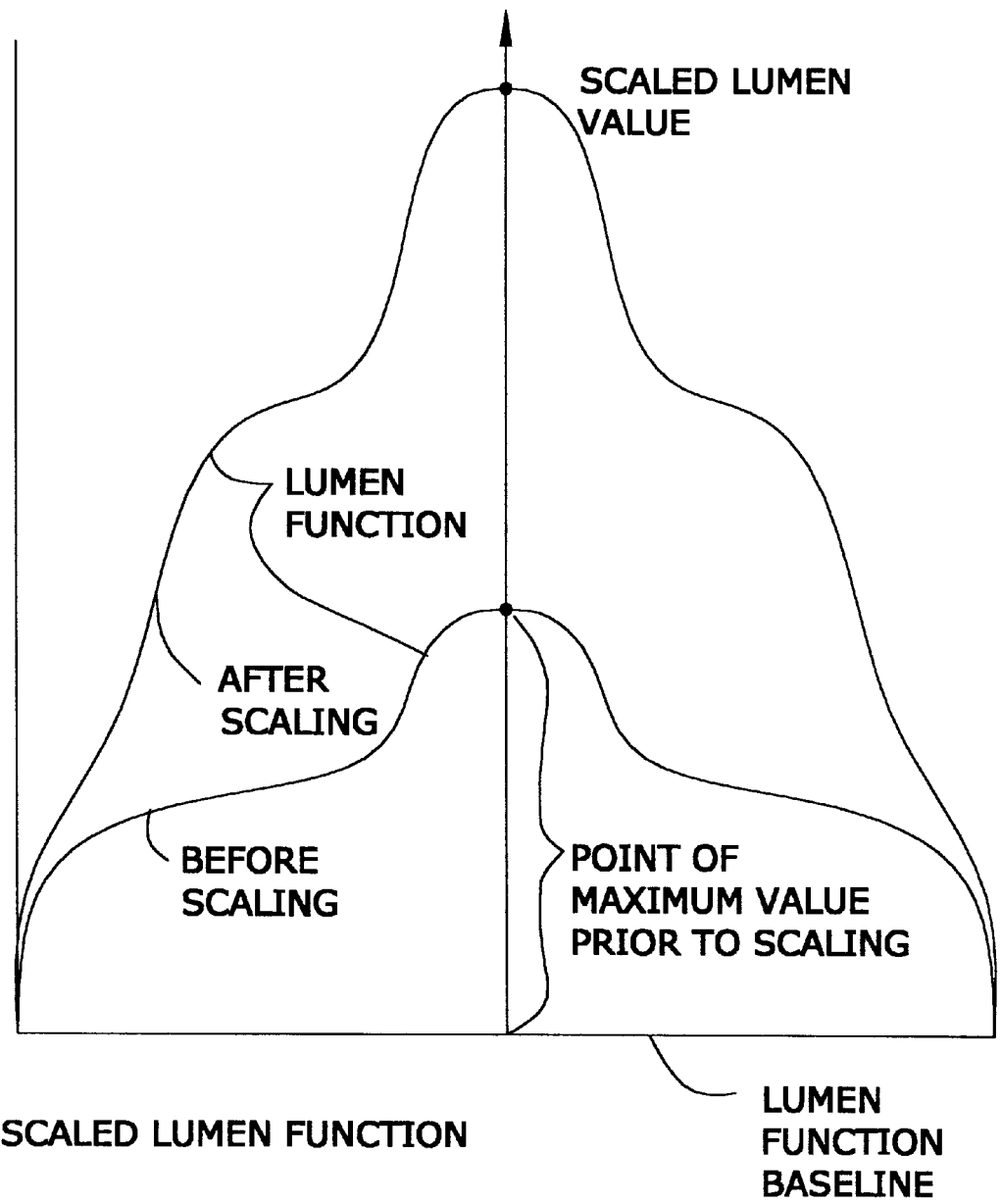
FIG. 10 shows an individually scaled lumen function.

Step 3: Adjusting the Initial Guess Section to Obtain Reconstructed Sections for Each Lumen Function The third step really performs the reconstruction of the artery image so as to determine the shape of the carotid arteries. Based on the scaled lumen functions I, II, III and IV of the X-rays, we modify the initial guess section in two different ways. The modifications result in two alternative reconstruction approaches: "upward reconstruction" and "downward reconstruction." Upward reconstruction is shown in FIG. 4(d). Downward reconstruction is shown in FIG. 4(e). To perform the reconstruction, we trace several rays from the lumen function baseline toward the initial guess section. The "lumen function baseline" is the straight line that extends from one end of the lumen function to the other. The lumen function base line is indicated in FIG. 10.

Figure 11:
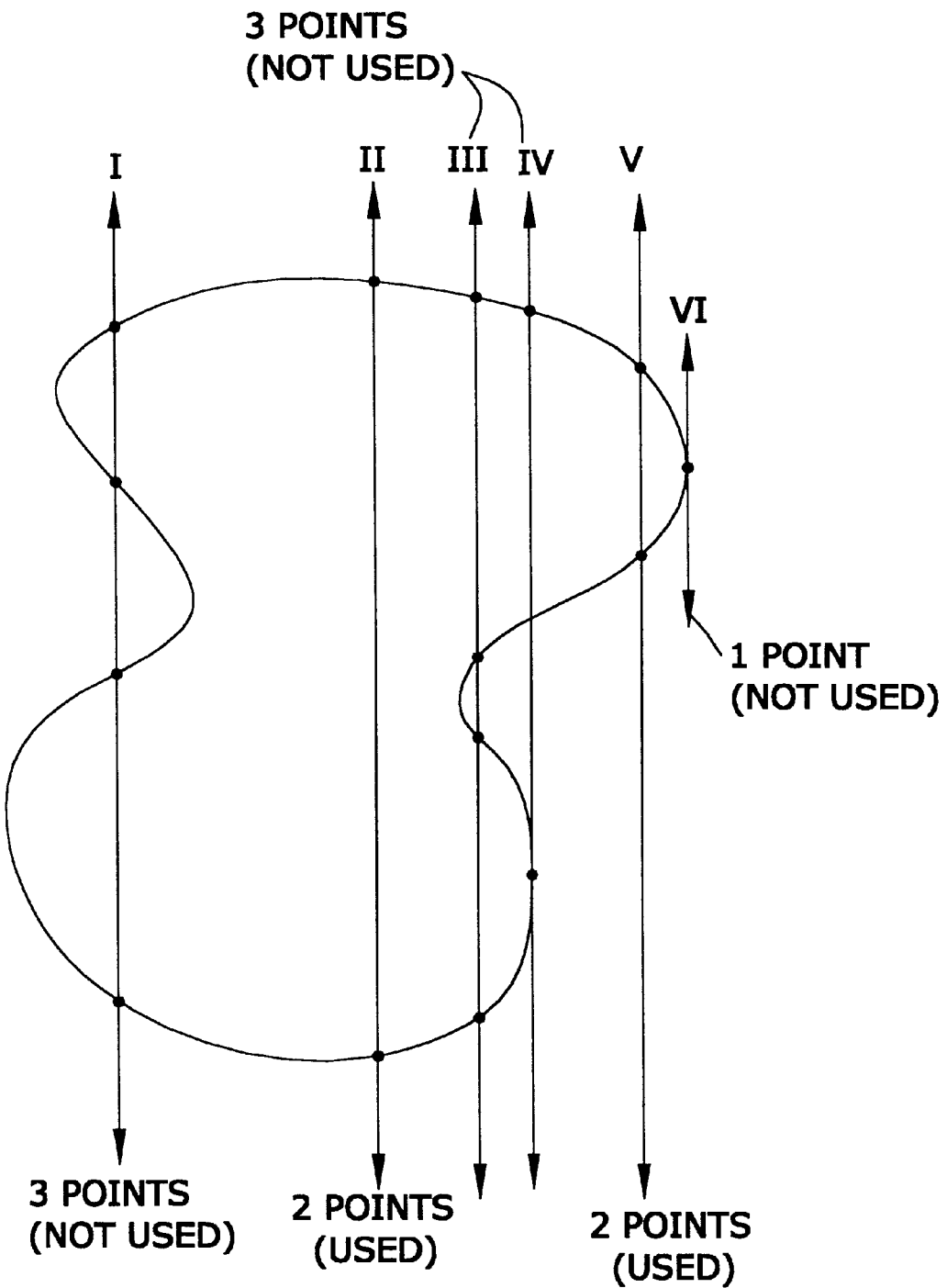
FIG. 11 shows rays intersecting only two points and rays intersecting more than two points.

During upward and downward reconstruction, if and only if a ray intersects the initial guess section at two points, we assume that ray travels a continuous distance across the unknown original cross-section. By "two points" we mean the two points along the boundary of the initial guess section. Rays intersecting only two points and rays intersecting more than two points is shown in FIG. 11. Then we use such a distance (the value of the scaled lumen function at that point) to modify the initial guess section.

For the upward reconstruction, we maintain the first intersection point and displace the second accordingly to the lumen function value. The first and second intersection point is shown in FIG. 4(d). Thus, the upward reconstruction creates the top of the carotid artery image. For the downward reconstruction, which can be seen in FIG. 4(e), we maintain the second intersection point and displace the first using the same lumen function. Thus, downward reconstruction creates the bottom of the carotid artery image. Thus, one lumen function, here the lumen function IV, is used to determine the shape of the top and the bottom of the arteries. FIGS. 4(d) and (e) illustrate how this works for the lumen function IV corresponding to the X-ray at 0°.

It should be noted that since the initial guess section 26 is convex as seen in FIG. 4(b) and FIG. 4(c), any ray can be used to reconstruct the initial guess section, as shown in FIGS. 4(d) and 4(e). There are no points of concavity in the initial section in FIG. 4(b) (which is substantially rectangular with rounded corners) which would cause a ray to intersect with the cross-section of the initial guess section more than two times.

For each upward and downward reconstructed section, we compute corresponding reconstructed lumen functions I, II, III and IV for each X-ray but the one used to obtain the reconstructed section itself Thus, as can be seen in FIG. 4(d), lumen function IV is being used to reconstruction the section. As that occurs, functions I, II, and III are reconstructed based on the reconstructed artery section image which was caused by the upward reconstruction of lumen function IV. The modified shape of lumen functions I, II, III are shown and overlap the original lumen functions to show the contrast in both FIGS. 4(d) and 4(e). We then compute the reconstruction error by comparing such reconstructed lumen function to the original ones.

Finally, the upward and downward reconstructions are blended to form yet a third reconstruction called the "blended reconstruction" which may be seen in FIG. 4(f). By "blending" it is meant taking the taking the images of one side and combining it with the images of another side to create a new image. The top image of the carotid arteries produced by upward construction as seen in FIG. 4(d) is combined with the bottom image of the carotid arteries produced by downward construction as seen in FIG. 4(e). The "blend factor" is computed taking into account the reconstruction errors of both blended sections. For this blended section, we similarly compute its reconstruction error by comparing its reconstructed lumen functions I, II, III and IV to the original ones.

Finally, among upward reconstruction, downward reconstruction, and blending, we choose the reconstructed guess section with the smallest error based upon the reconstructed lumen functions with the smallest deviance from the original lumen functions,. This is shown in FIGS. 4(d), 4(e) and 4(f). It is assumed that the reconstruction with the smallest error is the reconstructed section associated with that specific lumen function. Thus, if upward reconstruction as shown in FIG. 4(d) appears to have the smallest reconstruction image error, the transformed reconstructed guess section created by upward reconstruction as shown in FIG. 4(d) is selected. Likewise, if the downward reconstruction as shown in FIG. 4(e) appears to have the smallest reconstruction image error, the transformed reconstructed guess section created by downward reconstruction as shown in FIG. 4(d) is selected. Finally, if the blended reconstruction as shown in FIG. 4(f) appears to have the smallest reconstruction image error, the reconstructed guess section created by blending as shown in FIG. 4(f) is selected. FIGS. 4(d), 4(e) and 4(f) represent the first iteration.

This process as seen in FIGS. 4(d), 4(e) and 4(f) are repeated for the other lumen functions (not shown). The initial guess section is reconstructed with upward reconstruction, downward reconstruction and blending reconstruction for each respective lumen function.

Step 4: Choosing the Best Reconstructed Section

As seen, the IV lumen function is reconstructed using the information from the other lumen function. The lumen function IV as (as seen in FIGS. 4(d), 4(e) and 4(f), produced the best reconstruction of the initial guess section. Next, the same reconstruction is performed for the other lumen functions (I, II, and III). Each lumen function is reconstructed to generate twelve possible modified outlines. The best of the twelve possible outlines is selected. FIGS. 4(g), 4(h), and 4(i) show a second iteration for each lumen function, which represents the X-ray image at 90°. Subsequent iterations are not shown. The final reconstructed section will be taken from the iteration with the smallest error, considering all lumen-based reconstructions.

Step 5: Fine Tuning the Reconstruction By Picking the Best Reconstruction of All the Iterations Under Step 5, if the best reconstruction error of a given iteration is less than the reconstruction error of the previous iteration, the process continues. However, if the best reconstruction error of a given iteration is greater than the previous reconstruction error of the previous iteration, then the process stops and no more iterations are performed.

A third iteration would be performed if lumen functions of the second iteration were better than the first iteration. Then, the best reconstructed section of the second iteration would be used in the third iteration.

If a third iteration is performed, and the third iteration is better than the second iteration, the process is repeated and a fourth iteration occurs. If it is determined that the third iteration is better than the second, then the third iteration is input into the fourth iteration and it is asked if the fourth iteration is better than the third iteration, whereupon the fourth iteration is used to create the three dimensional model should it be better than the third. The third iteration is used to create the three dimensional model should it be better than the fourth iteration. If it is determined that the third iteration is not better than the second, the process stops and the reconstructed guess section of the second iteration is used.

In our illustrative example, after the first iteration, let us consider that the section in FIG. 4(f) is superior to the other eleven reconstructed section of the first iteration, based on the reconstruction error of the respective lumen functions. The computer program may halt at the first iteration or enter a second iteration, where the previous reconstructed section is assumed as the new initial guess section. FIGS. 4(g), 4(h), and 4(i) illustrate how, in the second iteration, the initial guess section (represented now by the section in Figure(f)) is modified to yield different reconstruction compared to the lumen function II (where scanning was done along the 90° axis). Note that the shaded area under the lumen function represents rays that intersect the initial guess section more than twice and so cannot be used in reconstructing the section. As a result, the section in FIG. 4(h) is close to the original section and, based on the reconstructed and original lumen functions comparison, would probably be chosen as the best reconstruction of the second iteration. Lumen function I, III and IV will also be tested against the first best reconstructed shape. Then, the best shape of the second iteration is compared to the first best shape. The computer program may enter another iteration to further fine tune the reconstruction. To stop the process, we use a "greedy approach": if an iteration gives worse results than the previous iteration, the computer program halts and uses reconstructed section of the previous iteration in the next iteration.

To gain smoothness, the reconstructed sections are represented by a curve known as a non-uniform B-spline. For a discussion on how the reconstructed sections may be represented by B-splines, see Farm, *Curves and Surfaces for Computer Aided Geometric Design*, Academic Press, New York (1988). The term "spline" goes back to long flexible strips of metal used by draftspersons to draw the curves of surfaces of airplanes, cars, and ships. A "spline curve" is a shape created when a user specifies a series of points and the computer software draws a curve that smoothly approaches these points. Splines may be described mathematically as polynomial functions which provide smooth curves with continuous first and second order derivatives. A spline is controlled by "control points." A control point is a point on the graph that exerts control over the way the graph is curved. If the control point moves, the shape of the curb moves. The curves have "knots" which are points where the curve changes direction. The lines between each knot are "curve segments" and may be described mathematically by some certain parameters. A "B-spline" is a type of spline which has a set of four control points having the property such that slope and curvature are continuous across the set of control points. In "uniform B-splines" there is uniform spacing between knots. In a "non-uniform B-spline" the spacing between knots is not uniform. As stated, the computer program makes use of non-uniform B-splines.

Further Considerations

It is important to note that the orientation of the X-rays in relation to the unknown cross-section may change the reconstruction accuracy. Thus, accuracy may vary according to the position of the X-ray imaging equipment. However, we have noticed that the computer program is in general capable of converging more than one image, possibly requiring more iterations.

Figure 5A:
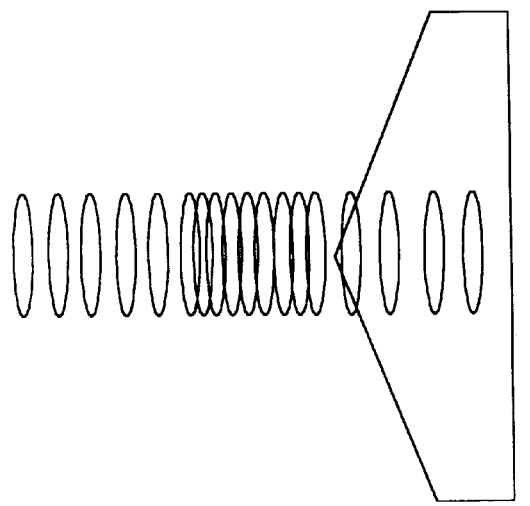
Figure 5D:
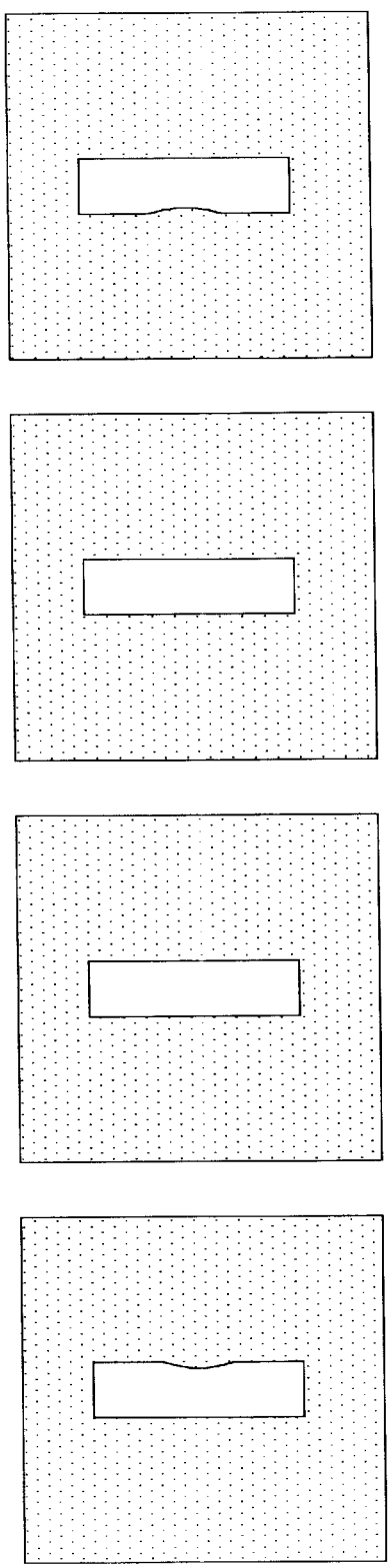

The computer program is extended so that multiple cross-sections, represented by different artery branches, can be reconstructed at the-same time. The advantage of creating multiple cross sections simultaneously, instead of reconstructing each cross-section separately, is that X-rays showing partially superimposed branches can still be used in the reconstruction process. These stacked cross-sections can be seen in FIG. 5(a). A "superimposed" image is a point where the image of one artery in an angiogram crosses the image of another artery in an angiogram. For instance, examine FIG. 5(d), showing simulated X-rays for a Y-shade model for when $\alpha=+90°$. There, there is a superimposed image since one artery branch is directly behind the other. When this occurs, it is not always clear whether one artery joins into another, or simply passes behind it. But, when multiple cross-sections are created simultaneously, as can be seen by using the images of $\alpha=-45°$. $\alpha=0°$ and $\alpha=+45°$, it can be seen that seen that the image of the arteries may be determined. We use the same principle: if a ray intersects the set of given cross-section only twice, its corresponding lumen value can be used in the reconstruction.

The Choice of a First Initial Guess Section

The proposed computer program works modifying an initial given cross-section. It is crucial to provide a good initial guess section so that reconstruction of complex shapes can be done with high accuracy. For convex shapes, shapes that share boundaries with their corresponding convex-hulls, or symmetric shapes, the use of an initial guess section computed based uniquely on the lumen function boundaries have brought adequate results. A "convex hull" is the smallest "convex set" (set which contain the entire line segment joining any pair of points) containing a given collection of points in a real linear space. A set is "convex" if for any two points in that set, the points on the straight line segment joining the two points are also contained in the set. For three-dimensional curves, in computer graphics, the convex hull is the convex polyhedron solid figure bounded by planar polygons formed by the control points. (A polygon is a planar figure having three or more straight sides such as a triangle, rectangle, pentagon, hexagon, heptagon, etc.) In three dimensional space, a convex hull may be thought of the polyhedron formed by stretching a rubber band around the four control points.

To create the initial guess section, we first compute the polygon defined by the intersections of the lumen boundaries and then compute-a non-uniform B-spline that fits well inside this polygon. This is amply seen in FIG. 4(b). The lumen boundaries of lumen functions I, II, III, and IV project out from the ends of the lumen functions along a line perpendicular to the baseline of the lumen functions. The lumen boundaries of lumen functions II and IV form a rectangle at their points of intersection. The boundaries of lumen functions I and III so to speak clip off the corners of the triangles, so that what is left is an octagon. The non-uniform B-spline is fit into the octagon as seen in FIG. 4(b) to obtain the initial guess section of the carotid arteries that is shown in FIG. 4(b).

Although ordinary carotid lesions are well represented by convex, partially convex, or symmetric shapes, complex shape reconstruction may also be required. This problem is solved by using coherency along the artery vertical axis. By "coherency" it is meant there is a fair amount of congruity or consistency between one section and another located near along the artery vertical axis. Three-dimensional arterial surfaces are in general smooth, and the difference between two consecutive cross-sections is small. Indeed, once we have an accurate reconstructed section, the best initial guess section for reconstructing the next cross-section is the section already reconstructed.

Preliminary Results

As a first test drive for the reconstruction computer program, we simulated an X-ray using a computer generated model and reconstructed the model based on such X-rays. The computer model surfaces were generated by interpolating several cross-section drawn at different vertical y coordinate. Each cross-section was hand-drawn using non-uniform B-splines. The interpolating mesh was also obtained through patches of B-splines. (The "interpolating mesh" as seen FIG. 5(b), may be thought of as the meshing that surrounds the known contours of the carotid artery sections so that a solid three-dimensional appearance. This interpolating mesh is created after all the layers have been determined. The computer constructs the interpolating mesh by constructing polygons that connect each contour to the contour above and below, so as to create a solid object. The interpolated mesh can also be called a "surface mesh." It is called an "interpolated mesh" because the position of the mesh (or image of the surface of the carotid arteries) is determined by interpolating the points between two carotid artery section images that are above and below each other. We used the attenuation projection to compute the simulated X-ray intensities, tracing rays from the virtual X-ray camera to the model and computing the sum of distances each ray traveled through the interior of the model. The virtual camera focal distance, the center-of-rotation distance, and the X-ray resolution were all defined based on typical X-ray equipment characteristics.

Figure 5E:
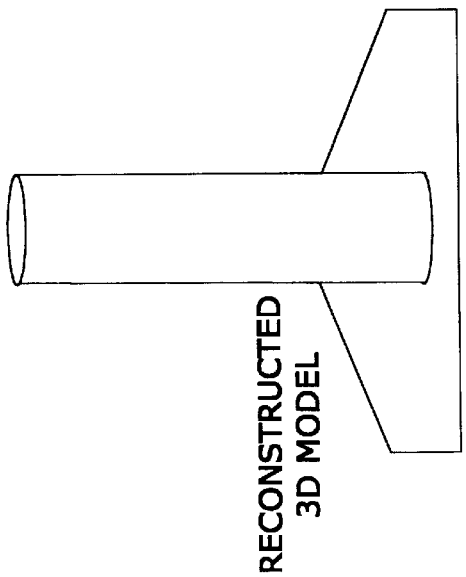

The first computer generated model represents a single branch of an artery with severe stenosis. FIG. 5(a) illustrates the cross-sections used to create the model. Each cross-section was reconstructed from lumen function of four orthoganal X-rays of an artery. FIG. 5(b) shows the interpolating mesh and FIG. 5(c) the obtained model rendered using a simple shading model. The simulated reconstructed X-rays taken from different angles are shown in FIG. 5(d). Such X-rays were then used as the input for the reconstruction computer program. The reconstructed model is illustrated in FIG. 5(e). It was obtained reconstructing just a few key-section and applying surface interpolation. Here, we did not use coherency among adjacent cross-sections; all reconstructed cross-section were obtained using an initial guess section computed from the lumen boundary intersections. FIG. 5(f) shows the comparison of reconstructed sections with some original key-sections (the grid step is 1 millimeter). As y=−0.8, there is no stenosis; as y=0, stenosis is very high.

Table 1 presents numerical results of the reconstruction. Notice that the artery orientation was chosen-so that the reconstruction would be harder; the C-shape of the artery lesion is not aligned with any X-ray projection. It is important to keep in mind that a reconstructed section can be computed for each line of the X-ray image. More detail in a reconstructed image is possible by taking cross-sectional densitometer lines closer to one another. Table 1 in FIG. 13 shows numerical results for thirteen sections taken along the y axis, one section at the stenosis (y=0) and six sections on either end of the stenosis. The actual area of each section and its error are compared to the computer reconstructed area and its error. The error measure can then be used to discard inaccurate reconstructions, creating an interpolating mesh that uses only reliable reconstructed sections.

Figure 6D:
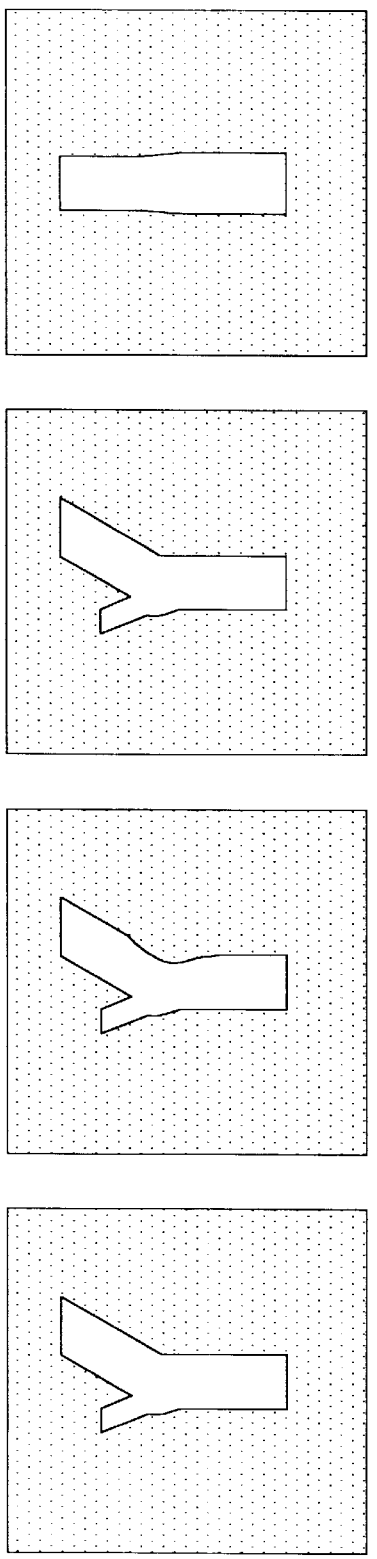
FIGS. 6(*a*) to 6(*i*) show the generation of a three dimensional image of the carotid arteries at an area of bifurcation created by interpolating the cross-sections of the artery.
Figure 6E:
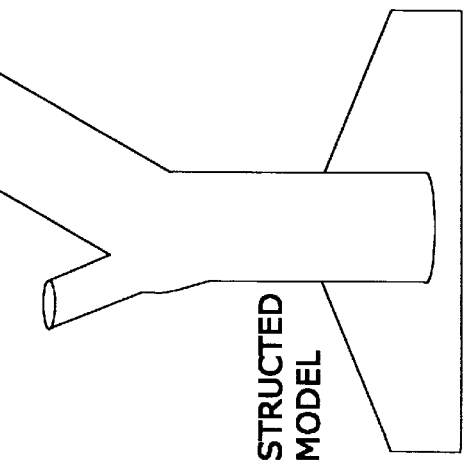
Figure 6F:
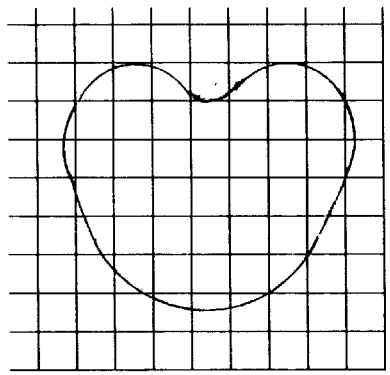
Figure 6F:
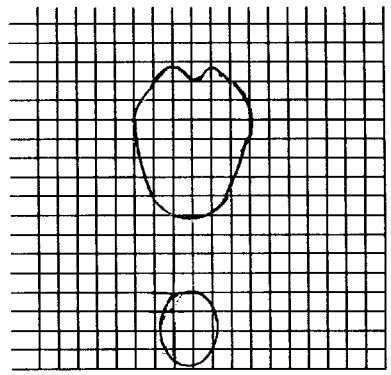
Figure 6F:
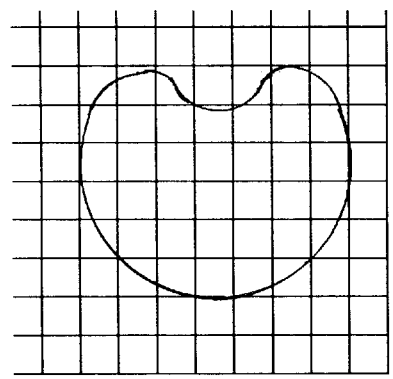
Figure 6F:
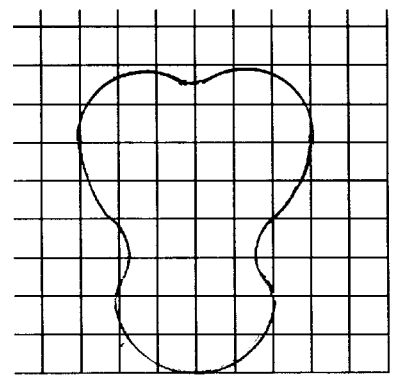
Figure 6F:
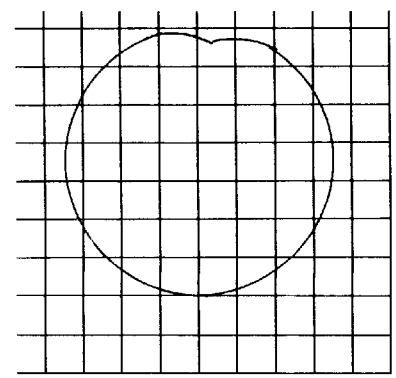
Figure 6F:
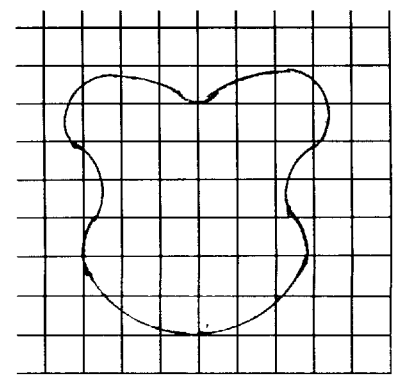

The second computer generated model represents a bifurcated artery model. Table 2 in FIG. 14 shows numerical results for another thirteen sections, with six sections on opposite sides of section v=0. The latter is chosen near the bifurcation. This example illustrates the capability of our approach in handling carotid stenosis formation at the point of bifurcation (FIG. 6 and Table 2). Again, the results could certainly be improved if vertical coherency were used to reconstruct adjacent cross-sections. A bifurcated artery is reconstructed as shown in FIGS. 6(a)–6(f). FIG. 6(d) shows images of the artery taken at zero degrees, ninety degrees, and plus or minus forty five degrees. FIG. 6(d) is the reconstructed 3-D model. FIG. 6(f) shows the cross-sections at different planar locations.

As noticed, both computer models were reconstructed with very high accuracy, especially if we compare such results to the methods currently begin used to predict carotid stenosis extent. These examples also prove that the perspective effects can in fact be ignored. The results presented in table 1 and table 2 also show that the reconstruction error reported by the computer program is an adequate parameter to judge the reconstruction accuracy without knowledge of the actual cross-section.

We claim:

1. A method for generating a three-dimensional shape of an artery comprising the steps of:
   obtaining a plurality of images at different angles so that each image defines the walls of the artery and comprises data representative of artery thickness;
   scanning the images to generate sets of lumen functions representative of thickness of the artery;
   iteratively reconstructing the lumen functions to create a three-dimensional image of the artery.
2. The method of claim 1 wherein:
   the images are X-ray images; and
   the data comprises data defining the walls of the artery.
3. The method of claim 2 wherein:
   the X-ray images are angiographic X-ray images.
4. The method of claim 2 wherein:
   the step of scanning the images comprises measuring the intensity variation of the X-ray's in each image.
5. The method of claim 1 wherein:
   the step of iteratively reconstructing further comprises:
      obtaining initial guess cross sections of the arteries,
      fitting the initial guess cross section into the boundaries of the lumen functions;
      adjusting the initial guess cross section in accordance with the lumen functions;
      scale the lumen functions in accordance with the adjusted initial guess cross section;
      and performing a first iterative reconstruction for each lumen function to generate first iterative reconstructed guess sections selecting and using a first lumen function to reconstruct the initial guess section, so as to perform a first iteration yielding a reconstructed guess section of the first iteration.
6. The method of claim 5 further comprising the steps of:
   selecting the first iterative reconstructed guess sections;
   performing one or more iterative reconstructions for each lumen functions to generate successive iterations of further reconstructed guess sections.
7. A method for generating a graphic three dimensional image of a portion of an artery comprising the steps of:
   capturing four X-ray images of the artery at four angles;
   dividing the images into a series of sequential cross-sectional planes spaced one from each other;
   for each plane, scanning each of the images to generate a lumen function for each of the four angles,
   choosing an initial outline image for each cross-section;
   selecting one of the four lumen functions;
   upwardly reconstructing a modified outline of the chosen outline image using the selected lumen function;
   reconstructing a first set of three lumen functions by comparing the upwardly modified outline to the respective three lumen functions and identifying the differences between the original and the reconstructed lumen functions;
   downwardly reconstructing a second modified outline of the chosen outline image using the selected lumen function;
   reconstructing a second set of three lumen functions by comparing the upwardly modified outline to the respective three lumen functions and identifying the differences between the original and the reconstructed lumen functions;
   blending the changes to the contours made in the first and second modified outlines to generate a third modified outline;
   reconstructing a third set of three lumen functions from the third modified outline by comparing each of the three lumen functions to the third modified outline;
   from among the resulting modified outlines, selecting the outline having the least cumulative differences between the reconstructed and original lumen functions; and
   aligning the selected images to generate a three dimensional graphic mesh image of the artery.
8. The method of claim 7 further comprising one or more iterations of the reconstructing steps using the selected outlines of the prior iterations.

9. The method of claim 8 further comprising the steps of:

representing the best reconstructed guess section amongst the first, second, third and fourth iterations by non-uniform B splines.

10. The method of claim 9 further comprising the steps of:

obtaining the X-ray images of multiple artery sections located one above each other so that they are stacked;

determining the interpolated mesh of the multiple carotid artery sections located one above each other.

11. An apparatus for determining three-dimensional artery section shape comprising:

a device for obtain an angiographic image of an artery cross section so that there are lines that define the walls of the artery, the lines that define the walls of the artery having data which represent varying degrees of X-ray intensity which correspond to artery thickness;

a means for gathering the data and using the data so that it can be used to determine artery shape so as to create a three-dimensional image of the artery;

a densitometer capable of measuring the X-ray intensity; and means for expressing the X-ray intensity for each X-ray image as lumen functions across an artery cross section.

* * * * *